United States Patent
Levin et al.

(10) Patent No.: US 8,906,045 B2
(45) Date of Patent: *Dec. 9, 2014

(54) ARTICULATING PATCH DEPLOYMENT DEVICE AND METHOD OF USE

(75) Inventors: Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 316 days.

This patent is subject to a terminal disclaimer.

(21) Appl. No.: 12/831,633

(22) Filed: Jul. 7, 2010

(65) Prior Publication Data

US 2011/0040311 A1    Feb. 17, 2011

Related U.S. Application Data

(60) Provisional application No. 61/234,320, filed on Aug. 17, 2009.

(51) Int. Cl.
| | |
|---|---|
| *A61B 17/00* | (2006.01) |
| *A61B 17/04* | (2006.01) |
| *A61B 17/068* | (2006.01) |
| *A61F 2/00* | (2006.01) |
| *A61B 17/29* | (2006.01) |

(52) U.S. Cl.
CPC ......... *A61B 17/068* (2013.01); *A61B 17/00491* (2013.01); *A61F 2002/0072* (2013.01); *A61B 17/0469* (2013.01); *A61B 2017/2927* (2013.01)
USPC .......................................... 606/151; 606/213

(58) Field of Classification Search
None
See application file for complete search history.

(56) References Cited

U.S. PATENT DOCUMENTS

| | | | |
|---|---|---|---|
| 4,347,847 A | 9/1982 | Usher | |
| 4,400,833 A | 8/1983 | Kurland | |
| 4,452,245 A | 6/1984 | Usher | |
| 4,485,816 A | 12/1984 | Krumme | |
| 4,585,458 A | 4/1986 | Kurland | |
| 4,633,873 A | 1/1987 | Dumican et al. | |
| 4,838,884 A | 6/1989 | Dumican et al. | |
| 4,854,316 A | 8/1989 | Davis | |
| 5,019,096 A | 5/1991 | Fox, Jr. et al. | |
| 5,116,357 A | 5/1992 | Eberbach | |
| 5,122,155 A | 6/1992 | Eberbach | |
| 5,125,553 A | 6/1992 | Oddsen et al. | |
| 5,141,515 A | 8/1992 | Eberbach | |
| 5,147,374 A | 9/1992 | Fernandez | |
| 5,176,692 A | 1/1993 | Wilk et al. | |
| 5,203,864 A | 4/1993 | Phillips | |
| 5,219,077 A | 6/1993 | Transue | |
| 5,249,682 A | 10/1993 | Transue | |

(Continued)

FOREIGN PATENT DOCUMENTS

| | | |
|---|---|---|
| CA | 2413904 A1 | 10/2003 |
| EP | 0328421 A2 | 8/1989 |

(Continued)

OTHER PUBLICATIONS

US 6,503,260, 01/2003, Schaller et al. (withdrawn).

*Primary Examiner* — Melanie Tyson
*Assistant Examiner* — Todd J Scherbel

(57) ABSTRACT

The invention generally relates to devices and methods for repairing an aperture in biological tissue. In certain embodiments, the invention provides devices and methods for deploying an implant to interact with biological tissue during a surgery.

20 Claims, 36 Drawing Sheets

(56) References Cited

U.S. PATENT DOCUMENTS

| | | | |
|---|---|---|---|
| 5,254,133 A | 10/1993 | Seid | |
| 5,258,000 A | 11/1993 | Gianturco | |
| 5,263,969 A | 11/1993 | Phillips | |
| 5,289,963 A | 3/1994 | McGarry et al. | |
| 5,290,217 A | 3/1994 | Campos | |
| 5,292,328 A | 3/1994 | Hain et al. | |
| 5,304,187 A | 4/1994 | Green et al. | |
| 5,333,624 A | 8/1994 | Tovey | |
| 5,354,292 A | 10/1994 | Braeuer et al. | |
| 5,356,064 A | 10/1994 | Green et al. | |
| 5,356,432 A | 10/1994 | Rutkow et al. | |
| 5,364,002 A | 11/1994 | Green et al. | |
| 5,364,004 A | 11/1994 | Davidson | |
| 5,366,460 A | 11/1994 | Eberbach | |
| 5,368,602 A | 11/1994 | de la Torre | |
| 5,370,650 A * | 12/1994 | Tovey et al. | 606/151 |
| 5,376,097 A | 12/1994 | Phillips | |
| 5,383,477 A * | 1/1995 | DeMatteis | 128/898 |
| 5,392,978 A | 2/1995 | Velez et al. | |
| 5,397,331 A | 3/1995 | Himpens et al. | |
| 5,405,360 A * | 4/1995 | Tovey | 606/151 |
| 5,425,357 A | 6/1995 | Moll et al. | |
| 5,425,740 A | 6/1995 | Hutchinson | |
| 5,433,996 A | 7/1995 | Kranzler et al. | |
| 5,464,403 A | 11/1995 | Kieturakis et al. | |
| 5,497,933 A | 3/1996 | Defonzo et al. | |
| 5,531,759 A | 7/1996 | Kensey et al. | |
| 5,560,224 A | 10/1996 | Tessler | |
| 5,560,532 A | 10/1996 | DeFonzo et al. | |
| 5,564,615 A | 10/1996 | Bishop et al. | |
| 5,569,273 A | 10/1996 | Titone et al. | |
| 5,577,654 A | 11/1996 | Bishop | |
| 5,588,580 A | 12/1996 | Paul et al. | |
| 5,588,581 A | 12/1996 | Conlon et al. | |
| 5,601,224 A | 2/1997 | Bishop et al. | |
| 5,614,284 A | 3/1997 | Kranzler et al. | |
| 5,618,290 A | 4/1997 | Toy et al. | |
| 5,626,587 A | 5/1997 | Bishop et al. | |
| 5,634,584 A | 6/1997 | Okorocha et al. | |
| 5,634,931 A | 6/1997 | Kugel | |
| 5,662,662 A | 9/1997 | Bishop et al. | |
| 5,695,525 A | 12/1997 | Mulhauser et al. | |
| 5,716,409 A | 2/1998 | Debbas | |
| 5,725,577 A | 3/1998 | Saxon | |
| 5,728,119 A | 3/1998 | Smith et al. | |
| 5,749,895 A | 5/1998 | Sawyer et al. | |
| 5,766,246 A | 6/1998 | Mulhauser et al. | |
| 5,769,864 A | 6/1998 | Kugel | |
| 5,779,728 A | 7/1998 | Lunsford et al. | |
| 5,803,902 A * | 9/1998 | Sienkiewicz et al. | 600/203 |
| 5,810,851 A | 9/1998 | Yoon | |
| 5,814,058 A | 9/1998 | Carlson et al. | |
| 5,817,109 A | 10/1998 | McGarry et al. | |
| 5,824,082 A | 10/1998 | Brown | |
| 5,836,961 A | 11/1998 | Kieturakis et al. | |
| 5,854,383 A | 12/1998 | Erneta et al. | |
| 5,863,531 A | 1/1999 | Naughton et al. | |
| 5,865,728 A | 2/1999 | Moll et al. | |
| 5,911,726 A | 6/1999 | Belknap | |
| 5,916,225 A | 6/1999 | Kugel | |
| 5,925,058 A | 7/1999 | Smith et al. | |
| 5,951,997 A | 9/1999 | Bezwada et al. | |
| 5,954,767 A | 9/1999 | Pajotin et al. | |
| 5,972,007 A | 10/1999 | Sheffield et al. | |
| 5,972,008 A | 10/1999 | Kalinski et al. | |
| 5,990,378 A | 11/1999 | Ellis | |
| 6,004,333 A | 12/1999 | Sheffield et al. | |
| 6,042,592 A | 3/2000 | Schmitt | |
| 6,066,776 A | 5/2000 | Goodwin et al. | |
| 6,066,777 A | 5/2000 | Benchetrit | |
| 6,090,116 A | 7/2000 | D'Aversa et al. | |
| 6,113,609 A | 9/2000 | Adams | |
| 6,113,611 A | 9/2000 | Allen et al. | |
| 6,113,624 A | 9/2000 | Bezwada et al. | |
| 6,156,045 A * | 12/2000 | Ulbrich et al. | 606/151 |
| 6,166,286 A | 12/2000 | Trabucco | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,197,036 B1 | 3/2001 | Tripp et al. | |
| 6,214,020 B1 | 4/2001 | Mulhauser et al. | |
| 6,224,616 B1 | 5/2001 | Kugel | |
| 6,241,768 B1 | 6/2001 | Agarwal et al. | |
| 6,258,113 B1 | 7/2001 | Adams et al. | |
| 6,258,124 B1 | 7/2001 | Darois et al. | |
| 6,267,772 B1 | 7/2001 | Mulhauser et al. | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,312,442 B1 | 11/2001 | Kieturakis et al. | |
| 6,319,264 B1 | 11/2001 | Tormala et al. | |
| 6,368,541 B1 | 4/2002 | Pajotin et al. | |
| 6,375,662 B1 | 4/2002 | Schmitt | |
| 6,383,201 B1 | 5/2002 | Dong | |
| 6,391,060 B1 | 5/2002 | Ory et al. | |
| 6,408,656 B1 | 6/2002 | Ory et al. | |
| 6,416,486 B1 | 7/2002 | Wampler | |
| 6,416,506 B1 * | 7/2002 | Tilton et al. | 606/1 |
| 6,425,900 B1 | 7/2002 | Knodel et al. | |
| 6,425,924 B1 | 7/2002 | Rousseau | |
| 6,436,030 B2 | 8/2002 | Rehil | |
| 6,447,524 B1 | 9/2002 | Knodel et al. | |
| 6,451,032 B1 * | 9/2002 | Ory et al. | 606/151 |
| 6,478,803 B1 * | 11/2002 | Kapec et al. | 606/151 |
| 6,485,503 B2 | 11/2002 | Jacobs et al. | |
| 6,497,650 B1 | 12/2002 | Nicolo | |
| 6,517,584 B1 | 2/2003 | Lecalve | |
| 6,527,785 B2 | 3/2003 | Sancoff et al. | |
| 6,551,241 B1 | 4/2003 | Schultz | |
| 6,551,333 B2 | 4/2003 | Kuhns et al. | |
| 6,558,400 B2 | 5/2003 | Deem et al. | |
| 6,565,590 B2 | 5/2003 | Kieturakis et al. | |
| 6,575,988 B2 | 6/2003 | Rousseau | |
| 6,607,541 B1 | 8/2003 | Gardiner et al. | |
| 6,610,006 B1 | 8/2003 | Amid et al. | |
| 6,613,059 B2 | 9/2003 | Schaller et al. | |
| 6,616,685 B2 | 9/2003 | Rousseau | |
| 6,638,208 B1 | 10/2003 | Natarajan et al. | |
| 6,638,284 B1 | 10/2003 | Rousseau et al. | |
| 6,638,292 B2 | 10/2003 | Adams | |
| 6,638,297 B1 | 10/2003 | Huitema | |
| 6,652,595 B1 | 11/2003 | Nicolo | |
| 6,666,817 B2 | 12/2003 | Li | |
| 6,669,706 B2 | 12/2003 | Schmitt et al. | |
| 6,669,735 B1 | 12/2003 | Pelissier | |
| 6,676,643 B2 | 1/2004 | Brushey | |
| 6,689,047 B2 | 2/2004 | Gellman | |
| 6,694,192 B2 | 2/2004 | Policker et al. | |
| 6,695,856 B2 | 2/2004 | Kieturakis et al. | |
| 6,709,442 B2 | 3/2004 | Miller et al. | |
| 6,736,823 B2 | 5/2004 | Darois et al. | |
| 6,736,854 B2 | 5/2004 | Vadurro et al. | |
| 6,737,371 B1 | 5/2004 | Planck et al. | |
| 6,746,458 B1 | 6/2004 | Cloud | |
| 6,755,867 B2 | 6/2004 | Rousseau | |
| 6,773,438 B1 | 8/2004 | Knodel et al. | |
| 6,783,554 B2 | 8/2004 | Amara et al. | |
| 6,790,213 B2 | 9/2004 | Cherok et al. | |
| 6,800,081 B2 | 10/2004 | Parodi | |
| 6,800,082 B2 | 10/2004 | Rousseau | |
| 6,805,669 B2 | 10/2004 | Swanbom | |
| 6,833,408 B2 | 12/2004 | Sehl et al. | |
| 6,837,893 B2 | 1/2005 | Miller | |
| 6,893,452 B2 | 5/2005 | Jacobs | |
| 6,913,607 B2 | 7/2005 | Ainsworth et al. | |
| 6,913,622 B2 | 7/2005 | Gjunter | |
| 6,936,052 B2 | 8/2005 | Gellman et al. | |
| 6,945,980 B2 | 9/2005 | Nguyen et al. | |
| 6,953,428 B2 | 10/2005 | Gellman et al. | |
| 6,960,217 B2 | 11/2005 | Bolduc | |
| 6,960,233 B1 | 11/2005 | Berg et al. | |
| 6,966,916 B2 | 11/2005 | Kumar | |
| 6,974,586 B2 | 12/2005 | Greenhalgh et al. | |
| 6,991,597 B2 | 1/2006 | Gellman et al. | |

(56) References Cited

U.S. PATENT DOCUMENTS

| | | |
|---|---|---|
| 7,001,405 B2 | 2/2006 | Kieturakis et al. |
| 7,011,688 B2 | 3/2006 | Gryska et al. |
| 7,025,772 B2 | 4/2006 | Gellman et al. |
| 7,049,345 B2 | 5/2006 | Holmes-Farley |
| 7,077,850 B2 | 7/2006 | Kortenbach |
| 7,083,629 B2 | 8/2006 | Weller et al. |
| 7,083,630 B2 | 8/2006 | DeVries et al. |
| 7,094,261 B2 | 8/2006 | Zotti et al. |
| 7,101,366 B2 | 9/2006 | Trout, III et al. |
| 7,101,381 B2 | 9/2006 | Ford et al. |
| 7,119,062 B1 | 10/2006 | Alvis et al. |
| 7,148,315 B2 | 12/2006 | Erneta et al. |
| 7,198,046 B1 | 4/2007 | Argenta et al. |
| 7,214,236 B2 | 5/2007 | Kieturakis et al. |
| 7,216,651 B2 | 5/2007 | Argenta et al. |
| 7,220,282 B2 | 5/2007 | Kuslich |
| 7,229,452 B2 | 6/2007 | Kayan |
| 7,235,043 B2 | 6/2007 | Gellman et al. |
| 7,235,295 B2 | 6/2007 | Laurencin et al. |
| 7,255,675 B2 | 8/2007 | Gertner et al. |
| 7,320,325 B2 | 1/2008 | Duchon et al. |
| 7,331,199 B2 | 2/2008 | Ory et al. |
| 7,381,225 B2 | 6/2008 | Croce et al. |
| 7,404,819 B1 | 7/2008 | Darios et al. |
| 7,406,969 B2 | 8/2008 | Duchon et al. |
| 7,407,480 B2 | 8/2008 | Staskin et al. |
| 7,491,232 B2 | 2/2009 | Bolduc et al. |
| 7,500,945 B2 | 3/2009 | Cox et al. |
| 7,500,993 B2 | 3/2009 | De La Torre et al. |
| 7,524,333 B2 | 4/2009 | Lambrecht et al. |
| 7,544,213 B2 | 6/2009 | Adams |
| 7,553,329 B2 | 6/2009 | Lambrecht et al. |
| 7,553,330 B2 | 6/2009 | Lambrecht et al. |
| RE40,833 E | 7/2009 | Wintermantel et al. |
| 7,566,337 B2 | 7/2009 | Sogaard-Andersen et al. |
| 7,594,921 B2 | 9/2009 | Browning |
| 7,601,118 B2 | 10/2009 | Smith et al. |
| 7,601,172 B2 | 10/2009 | Segal et al. |
| 7,947,054 B2 * | 5/2011 | Eldar et al. .................. 606/151 |
| 8,097,008 B2 * | 1/2012 | Henderson .................. 606/151 |
| 8,753,359 B2 * | 6/2014 | Levin et al. .................. 606/151 |
| 2001/0016754 A1 | 8/2001 | Adams et al. |
| 2001/0018592 A1 | 8/2001 | Schaller et al. |
| 2001/0018593 A1 | 8/2001 | Nguyen et al. |
| 2001/0027347 A1 | 10/2001 | Rousseau |
| 2001/0044637 A1 | 11/2001 | Jacobs et al. |
| 2001/0049538 A1 | 12/2001 | Trabucco |
| 2001/0049539 A1 | 12/2001 | Rehil |
| 2001/0053919 A1 | 12/2001 | Kieturakis et al. |
| 2001/0056275 A1 | 12/2001 | Brushey |
| 2002/0010457 A1 | 1/2002 | Duchon et al. |
| 2002/0010480 A1 | 1/2002 | Sancoff et al. |
| 2002/0010490 A1 | 1/2002 | Schaller et al. |
| 2002/0010494 A1 | 1/2002 | Policker et al. |
| 2002/0029048 A1 | 3/2002 | Miller |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0058967 A1 | 5/2002 | Jervis |
| 2002/0065524 A1 | 5/2002 | Miller et al. |
| 2002/0066360 A1 | 6/2002 | Greenhalgh et al. |
| 2002/0077652 A1 | 6/2002 | Kieturakis et al. |
| 2002/0082621 A1 | 6/2002 | Schurr et al. |
| 2002/0087170 A1 | 7/2002 | Kuhns et al. |
| 2002/0091405 A1 | 7/2002 | Kieturakis et al. |
| 2002/0103434 A1 | 8/2002 | Swanbom |
| 2002/0103494 A1 | 8/2002 | Pacey |
| 2002/0107539 A1 | 8/2002 | Kieturakis et al. |
| 2002/0116070 A1 | 8/2002 | Amara et al. |
| 2002/0117534 A1 | 8/2002 | Green et al. |
| 2002/0147457 A1 | 10/2002 | Rousseau |
| 2002/0165561 A1 | 11/2002 | Ainsworth et al. |
| 2002/0169452 A1 | 11/2002 | Tormala et al. |
| 2002/0173803 A1 | 11/2002 | Ainsworth et al. |
| 2002/0173804 A1 | 11/2002 | Rousseau |
| 2002/0183765 A1 | 12/2002 | Adams |
| 2002/0183768 A1 | 12/2002 | Deem et al. |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller et al. |
| 2003/0073976 A1 | 4/2003 | Brushey |
| 2003/0078602 A1 | 4/2003 | Rousseau |
| 2003/0078603 A1 | 4/2003 | Schaller et al. |
| 2003/0105473 A1 | 6/2003 | Miller |
| 2003/0109892 A1 | 6/2003 | Deem et al. |
| 2003/0119985 A1 | 6/2003 | Sehl et al. |
| 2003/0120265 A1 | 6/2003 | Deem et al. |
| 2003/0120299 A1 | 6/2003 | Kieturakis et al. |
| 2003/0130745 A1 | 7/2003 | Cherok et al. |
| 2003/0166628 A1 | 9/2003 | Doyle et al. |
| 2003/0171761 A1 | 9/2003 | Sancoff et al. |
| 2003/0171812 A1 | 9/2003 | Grunberg et al. |
| 2003/0171823 A1 | 9/2003 | Zotti et al. |
| 2003/0187516 A1 | 10/2003 | Amid et al. |
| 2003/0195531 A1 | 10/2003 | Gardiner et al. |
| 2003/0208211 A1 | 11/2003 | Kortenbach |
| 2003/0212460 A1 | 11/2003 | Darois et al. |
| 2003/0212461 A1 | 11/2003 | Vadurro et al. |
| 2003/0212462 A1 | 11/2003 | Gryska et al. |
| 2003/0220660 A1 | 11/2003 | Kortenbach et al. |
| 2003/0225355 A1 | 12/2003 | Butler |
| 2003/0225420 A1 | 12/2003 | Wardle |
| 2004/0002679 A1 | 1/2004 | Trout et al. |
| 2004/0010317 A1 | 1/2004 | Lambrecht et al. |
| 2004/0019360 A1 | 1/2004 | Farnsworth et al. |
| 2004/0024386 A1 | 2/2004 | Deem et al. |
| 2004/0024465 A1 | 2/2004 | Lambrecht et al. |
| 2004/0030217 A1 | 2/2004 | Yeung et al. |
| 2004/0039453 A1 | 2/2004 | Anderson et al. |
| 2004/0044364 A1 | 3/2004 | DeVries et al. |
| 2004/0044412 A1 | 3/2004 | Lambrecht et al. |
| 2004/0049227 A1 | 3/2004 | Jervis |
| 2004/0049282 A1 | 3/2004 | Gjunter |
| 2004/0054376 A1 | 3/2004 | Ory et al. |
| 2004/0059356 A1 | 3/2004 | Gingas |
| 2004/0064131 A1 | 4/2004 | Brushey |
| 2004/0073237 A1 | 4/2004 | Leinsing |
| 2004/0073257 A1 | 4/2004 | Spitz |
| 2004/0082755 A1 | 4/2004 | Erneta et al. |
| 2004/0087970 A1 | 5/2004 | Chu et al. |
| 2004/0087979 A1 | 5/2004 | Field et al. |
| 2004/0087980 A1 | 5/2004 | Ford et al. |
| 2004/0092937 A1 | 5/2004 | Criscuolo et al. |
| 2004/0092969 A1 | 5/2004 | Kumar |
| 2004/0092970 A1 | 5/2004 | Xavier |
| 2004/0097924 A1 | 5/2004 | Lambrecht et al. |
| 2004/0097986 A1 | 5/2004 | Adams |
| 2004/0122452 A1 | 6/2004 | Deem et al. |
| 2004/0122453 A1 | 6/2004 | Deem et al. |
| 2004/0133214 A1 | 7/2004 | Kayan |
| 2004/0144395 A1 | 7/2004 | Evans et al. |
| 2004/0152977 A1 | 8/2004 | Duchon et al. |
| 2004/0152978 A1 | 8/2004 | Duchon et al. |
| 2004/0172048 A1 | 9/2004 | Browning |
| 2004/0181288 A1 | 9/2004 | Darois et al. |
| 2004/0193043 A1 | 9/2004 | Duchon et al. |
| 2004/0215219 A1 | 10/2004 | Eldridge et al. |
| 2004/0225247 A1 | 11/2004 | Pugsley et al. |
| 2004/0225373 A1 | 11/2004 | Pugsley et al. |
| 2004/0230208 A1 | 11/2004 | Shayani |
| 2004/0234576 A1 | 11/2004 | Martin et al. |
| 2004/0249412 A1 | 12/2004 | Snow et al. |
| 2004/0254592 A1 | 12/2004 | DiCarlo et al. |
| 2005/0004427 A1 | 1/2005 | Cervigni |
| 2005/0010239 A1 | 1/2005 | Chefitz |
| 2005/0010306 A1 | 1/2005 | Priewe et al. |
| 2005/0015102 A1 | 1/2005 | Chefitz |
| 2005/0019436 A1 | 1/2005 | Burch et al. |
| 2005/0021058 A1 | 1/2005 | Negro |
| 2005/0027369 A1 | 2/2005 | Eldridge et al. |
| 2005/0033318 A1 | 2/2005 | Miller et al. |

(56) References Cited

U.S. PATENT DOCUMENTS

| | | |
|---|---|---|
| 2005/0038452 A1 | 2/2005 | Chu |
| 2005/0054771 A1 | 3/2005 | Sehl et al. |
| 2005/0055097 A1 | 3/2005 | Grunberg et al. |
| 2005/0060038 A1 | 3/2005 | Lambrecht et al. |
| 2005/0065072 A1 | 3/2005 | Keeler et al. |
| 2005/0075667 A1 | 4/2005 | Schaller et al. |
| 2005/0080454 A1 | 4/2005 | Drews et al. |
| 2005/0113849 A1 | 5/2005 | Popadiuk et al. |
| 2005/0113858 A1 | 5/2005 | Deutsch |
| 2005/0118239 A1 | 6/2005 | Sabesan |
| 2005/0129733 A1 | 6/2005 | Milbocker et al. |
| 2005/0142315 A1 | 6/2005 | DeSimone et al. |
| 2005/0143817 A1 | 6/2005 | Hunter et al. |
| 2005/0149072 A1 | 7/2005 | DeVries et al. |
| 2005/0149080 A1 | 7/2005 | Hunter et al. |
| 2005/0149158 A1 | 7/2005 | Hunter et al. |
| 2005/0154361 A1 | 7/2005 | Sabesan |
| 2005/0159777 A1 | 7/2005 | Spitz |
| 2005/0165425 A1 | 7/2005 | Croce et al. |
| 2005/0165488 A1 | 7/2005 | Hunter et al. |
| 2005/0169959 A1 | 8/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0183728 A1 | 8/2005 | Hunter et al. |
| 2005/0191331 A1 | 9/2005 | Hunter et al. |
| 2005/0192600 A1 | 9/2005 | Nicolo et al. |
| 2005/0202067 A1 | 9/2005 | Lendlein et al. |
| 2005/0222591 A1 | 10/2005 | Gingras et al. |
| 2005/0228408 A1 | 10/2005 | Fricke et al. |
| 2005/0234557 A1 | 10/2005 | Lambrecht et al. |
| 2005/0240269 A1 | 10/2005 | Lambrecht et al. |
| 2005/0244455 A1 | 11/2005 | Greenawalt |
| 2005/0245787 A1 | 11/2005 | Cox et al. |
| 2005/0249770 A1 | 11/2005 | Hunter |
| 2005/0267325 A1 | 12/2005 | Bouchier et al. |
| 2005/0271794 A1 | 12/2005 | DeSimone et al. |
| 2005/0273146 A1 | 12/2005 | DeSimone et al. |
| 2005/0283189 A1 | 12/2005 | Rosenblatt |
| 2005/0283190 A1 | 12/2005 | Huitema et al. |
| 2005/0283246 A1 | 12/2005 | Cauthen et al. |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1 | 1/2006 | Modesitt |
| 2006/0015142 A1 | 1/2006 | Malazgirt |
| 2006/0015143 A1 | 1/2006 | Alvarado |
| 2006/0024238 A1 | 2/2006 | Barth et al. |
| 2006/0025649 A1 | 2/2006 | Smith et al. |
| 2006/0039896 A1 | 2/2006 | Kleinsek et al. |
| 2006/0047180 A1 | 3/2006 | Hegde et al. |
| 2006/0052816 A1 | 3/2006 | Bates et al. |
| 2006/0064175 A1 | 3/2006 | Pelissier et al. |
| 2006/0079558 A1 | 4/2006 | Aberg et al. |
| 2006/0079559 A1 | 4/2006 | Aberg et al. |
| 2006/0083710 A1 | 4/2006 | Joerger et al. |
| 2006/0105026 A1 | 5/2006 | Fortune et al. |
| 2006/0116696 A1 | 6/2006 | Odermatt et al. |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0142787 A1 | 6/2006 | Weller et al. |
| 2006/0147488 A1 | 7/2006 | Wohlert |
| 2006/0147492 A1 | 7/2006 | Hunter et al. |
| 2006/0149316 A1 | 7/2006 | DeVries et al. |
| 2006/0155165 A1 | 7/2006 | Vanden Hoek et al. |
| 2006/0155379 A1 | 7/2006 | Heneveld et al. |
| 2006/0177489 A1 | 8/2006 | Massouda et al. |
| 2006/0189918 A1 | 8/2006 | Barker |
| 2006/0200246 A1 | 9/2006 | Lambrecht et al. |
| 2006/0206118 A1 | 9/2006 | Kim et al. |
| 2006/0206178 A1 | 9/2006 | Kim |
| 2006/0210602 A1 | 9/2006 | Sehl et al. |
| 2006/0217812 A1 | 9/2006 | Lambrecht et al. |
| 2006/0228391 A1 | 10/2006 | Seyedin et al. |
| 2006/0233852 A1 | 10/2006 | Milbocker |
| 2006/0240063 A9 | 10/2006 | Hunter et al. |
| 2006/0251702 A1 | 11/2006 | Janis et al. |
| 2006/0253203 A1 | 11/2006 | Alvarado |
| 2006/0264698 A1 | 11/2006 | Kondonis et al. |
| 2006/0282103 A1 | 12/2006 | Fricke et al. |
| 2006/0282105 A1 | 12/2006 | Ford et al. |
| 2006/0287729 A1 | 12/2006 | Segal et al. |
| 2006/0287730 A1 | 12/2006 | Segal et al. |
| 2007/0016300 A1 | 1/2007 | Kuslich |
| 2007/0021756 A1 | 1/2007 | Kortenbach |
| 2007/0026043 A1 | 2/2007 | Guan et al. |
| 2007/0027358 A1 | 2/2007 | Gertner et al. |
| 2007/0032881 A1 | 2/2007 | Browning |
| 2007/0036876 A1 | 2/2007 | Burch et al. |
| 2007/0038220 A1 | 2/2007 | Shipp |
| 2007/0038310 A1 | 2/2007 | Guetty |
| 2007/0100355 A1 | 5/2007 | Bonde et al. |
| 2007/0110786 A1 | 5/2007 | Tenney et al. |
| 2007/0111937 A1 | 5/2007 | Pickar et al. |
| 2007/0112361 A1* | 5/2007 | Schonholz et al. ........... 606/151 |
| 2007/0118133 A1 | 5/2007 | Lambrecht et al. |
| 2007/0118158 A1 | 5/2007 | Deem et al. |
| 2007/0118159 A1 | 5/2007 | Deem et al. |
| 2007/0122425 A1 | 5/2007 | Keeler et al. |
| 2007/0134292 A1 | 6/2007 | Suokas et al. |
| 2007/0135929 A1 | 6/2007 | Williams et al. |
| 2007/0156245 A1 | 7/2007 | Cauthen et al. |
| 2007/0162030 A1 | 7/2007 | Aranyi et al. |
| 2007/0162135 A1 | 7/2007 | Segal et al. |
| 2007/0167963 A1 | 7/2007 | Deem et al. |
| 2007/0173864 A1 | 7/2007 | Chu |
| 2007/0173888 A1 | 7/2007 | Gertner et al. |
| 2007/0179335 A1 | 8/2007 | Gertner et al. |
| 2007/0184277 A1 | 8/2007 | Schussler et al. |
| 2007/0185506 A1 | 8/2007 | Jackson |
| 2007/0185541 A1 | 8/2007 | DiUbaldi et al. |
| 2007/0198040 A1 | 8/2007 | Buevich et al. |
| 2007/0202148 A1 | 8/2007 | Ringeisen et al. |
| 2007/0202173 A1 | 8/2007 | Cueto-Garcia |
| 2007/0203507 A1 | 8/2007 | McLaughlin et al. |
| 2007/0207186 A1 | 9/2007 | Scanlon et al. |
| 2007/0208358 A1 | 9/2007 | Kayan |
| 2007/0219569 A1 | 9/2007 | Shayani |
| 2007/0225791 A1 | 9/2007 | Molitor et al. |
| 2007/0244502 A1 | 10/2007 | Deutsch |
| 2007/0250147 A1 | 10/2007 | Walther et al. |
| 2007/0260179 A1 | 11/2007 | Sholev et al. |
| 2007/0260268 A1 | 11/2007 | Bartee et al. |
| 2007/0265710 A1 | 11/2007 | Brown et al. |
| 2007/0270752 A1 | 11/2007 | LaBombard |
| 2007/0280990 A1 | 12/2007 | Stopek |
| 2007/0293717 A1 | 12/2007 | Kaleta et al. |
| 2007/0293878 A1 | 12/2007 | Butsch |
| 2007/0299300 A1 | 12/2007 | Smith et al. |
| 2007/0299542 A1 | 12/2007 | Mathisen et al. |
| 2008/0015501 A1 | 1/2008 | Gertner |
| 2008/0021545 A1 | 1/2008 | Reneker et al. |
| 2008/0033461 A1 | 2/2008 | Koeckerling et al. |
| 2008/0035243 A1 | 2/2008 | Breitenkamp et al. |
| 2008/0045952 A1 | 2/2008 | Kuslich |
| 2008/0065229 A1 | 3/2008 | Adams |
| 2008/0086216 A1 | 4/2008 | Wilson et al. |
| 2008/0091222 A1 | 4/2008 | Deusch et al. |
| 2008/0091276 A1 | 4/2008 | Deusch et al. |
| 2008/0103351 A1 | 5/2008 | Montpetit et al. |
| 2008/0113035 A1 | 5/2008 | Hunter |
| 2008/0125869 A1 | 5/2008 | Paz et al. |
| 2008/0131509 A1 | 6/2008 | Hossainy et al. |
| 2008/0132602 A1 | 6/2008 | Rizk et al. |
| 2008/0147198 A1 | 6/2008 | Cherok et al. |
| 2008/0147200 A1 | 6/2008 | Rousseau et al. |
| 2008/0167519 A1 | 7/2008 | St-Germain |
| 2008/0167667 A1 | 7/2008 | Criscuolo et al. |
| 2008/0167668 A1 | 7/2008 | Criscuolo et al. |
| 2008/0188874 A1* | 8/2008 | Henderson .................... 606/151 |

(56) References Cited

U.S. PATENT DOCUMENTS

| | | |
|---|---|---|
| 2008/0193494 A1 | 8/2008 | Sabesan |
| 2008/0195121 A1 | 8/2008 | Eldar et al. |
| 2008/0200979 A1 | 8/2008 | Dieck et al. |
| 2008/0215154 A1 | 9/2008 | Lambrecht et al. |
| 2008/0243149 A1 | 10/2008 | Kockerling et al. |
| 2008/0255593 A1 | 10/2008 | St-Germain |
| 2008/0260794 A1 | 10/2008 | Lauritzen et al. |
| 2008/0269896 A1 | 10/2008 | Cherok et al. |
| 2008/0281433 A1 | 11/2008 | Chang et al. |
| 2008/0287970 A1 | 11/2008 | Amato et al. |
| 2008/0306497 A1 | 12/2008 | Brown et al. |
| 2008/0312751 A1 | 12/2008 | Pugsley et al. |
| 2009/0004239 A1 | 1/2009 | Ladet et al. |
| 2009/0005867 A1 | 1/2009 | Lefranc et al. |
| 2009/0012350 A1 | 1/2009 | Tihon |
| 2009/0012546 A1 | 1/2009 | N'diaye et al. |
| 2009/0018559 A1 | 1/2009 | Buevich et al. |
| 2009/0030434 A1 | 1/2009 | Paz et al. |
| 2009/0030522 A1 | 1/2009 | Cauthen, III et al. |
| 2009/0030527 A1 | 1/2009 | Richter |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0036996 A1 | 2/2009 | Roeber |
| 2009/0062823 A1 | 3/2009 | Richter |
| 2009/0069826 A1 | 3/2009 | Walther et al. |
| 2009/0105526 A1 | 4/2009 | Piroli Torelli et al. |
| 2009/0125041 A1 | 5/2009 | Dudai |
| 2009/0137864 A1 | 5/2009 | Cox et al. |
| 2009/0149875 A1 | 6/2009 | Abele et al. |
| 2009/0155332 A1 | 6/2009 | Sherry et al. |
| 2009/0157184 A1 | 6/2009 | Cauthen, III et al. |
| 2009/0157195 A1 | 6/2009 | Siedle |
| 2009/0162273 A1 | 6/2009 | Lawrynowicz et al. |
| 2009/0182190 A1 | 7/2009 | Dann |
| 2009/0182352 A1 | 7/2009 | Paz et al. |
| 2009/0187258 A1 | 7/2009 | Ip et al. |
| 2009/0192346 A1 | 7/2009 | Rosenblatt |
| 2009/0192528 A1 | 7/2009 | Higgins et al. |
| 2009/0198260 A1 | 8/2009 | Ford et al. |
| 2009/0204130 A1 | 8/2009 | Kantsevoy et al. |
| 2009/0204227 A1 | 8/2009 | Derwin et al. |
| 2009/0216075 A1 | 8/2009 | Bell et al. |
| 2009/0216104 A1 | 8/2009 | DeSimone et al. |
| 2009/0216264 A1* | 8/2009 | Friedman et al. .............. 606/213 |
| 2009/0216338 A1 | 8/2009 | Gingas et al. |
| 2009/0234379 A1 | 9/2009 | Rehnke |
| 2009/0234461 A1 | 9/2009 | Rehnke |
| 2009/0240342 A1 | 9/2009 | Lindh et al. |
| 2009/0240343 A1 | 9/2009 | Adams |
| 2009/0248048 A1 | 10/2009 | Milbocker |
| 2009/0254103 A1 | 10/2009 | Deutsch |
| 2009/0259094 A1 | 10/2009 | Bouchier et al. |
| 2009/0281563 A1 | 11/2009 | Newell et al. |
| 2010/0069930 A1 | 3/2010 | Roslin et al. |
| 2012/0209401 A1* | 8/2012 | Euteneuer et al. ......... 623/23.72 |
| 2013/0018395 A1* | 1/2013 | Friedlander et al. .......... 606/151 |

FOREIGN PATENT DOCUMENTS

| | | |
|---|---|---|
| EP | 0525791 A1 | 2/1993 |
| EP | 0537769 A1 | 4/1993 |
| EP | 0544485 A1 | 6/1993 |
| EP | 0556018 A1 | 8/1993 |
| EP | 0557963 A1 | 9/1993 |
| EP | 0557964 A1 | 9/1993 |
| EP | 0573273 A2 | 12/1993 |
| EP | 0579377 A2 | 1/1994 |
| EP | 0581036 A1 | 2/1994 |
| EP | 0614650 A2 | 9/1994 |
| EP | 0702934 A1 | 3/1996 |
| EP | 0744162 A2 | 11/1996 |
| EP | 0581036 | 1/1997 |
| EP | 0519022 B1 | 12/1997 |
| EP | 0827724 A2 | 3/1998 |
| EP | 0553344 B1 | 9/1998 |
| EP | 0746258 B1 | 9/1998 |
| EP | 0898944 A2 | 3/1999 |
| EP | 0908482 A1 | 4/1999 |
| EP | 0986993 A1 | 3/2000 |
| EP | 0837660 B1 | 5/2000 |
| EP | 1060714 A2 | 12/2000 |
| EP | 1145693 A2 | 10/2001 |
| EP | 1181899 A2 | 2/2002 |
| EP | 1199037 A2 | 4/2002 |
| EP | 1199038 A2 | 4/2002 |
| EP | 1219265 A2 | 7/2002 |
| EP | 0746267 B1 | 11/2002 |
| EP | 1018980 B1 | 1/2003 |
| EP | 1306061 A2 | 5/2003 |
| EP | 1317904 A1 | 6/2003 |
| EP | 1366717 A1 | 12/2003 |
| EP | 0783270 B1 | 6/2004 |
| EP | 1200010 B1 | 3/2005 |
| EP | 1164967 B1 | 5/2005 |
| EP | 1541183 A1 | 6/2005 |
| EP | WO2005082273 A1 | 9/2005 |
| EP | 0828453 B1 | 11/2005 |
| EP | 1001717 B1 | 11/2005 |
| EP | 1303230 B1 | 11/2005 |
| EP | 1607048 A1 | 12/2005 |
| EP | 1404250 B1 | 2/2006 |
| EP | 1671604 A2 | 6/2006 |
| EP | 1674048 A1 | 6/2006 |
| EP | 1274473 B1 | 7/2006 |
| EP | 0934024 B1 | 8/2006 |
| EP | 1503683 B1 | 8/2006 |
| EP | 1700579 A1 | 9/2006 |
| EP | 1704832 A2 | 9/2006 |
| EP | 200614650 A2 | 10/2006 |
| EP | 1079741 B1 | 11/2006 |
| EP | 0964645 B1 | 7/2007 |
| EP | 1163019 B1 | 10/2007 |
| EP | 1849440 A1 | 10/2007 |
| EP | 1867348 A2 | 12/2007 |
| EP | 1870056 A1 | 12/2007 |
| EP | 1531739 B1 | 2/2008 |
| EP | 1406557 B1 | 11/2008 |
| EP | 1990014 A2 | 11/2008 |
| EP | 2002800 A1 | 12/2008 |
| EP | 1505927 B1 | 1/2009 |
| EP | 1372525 B1 | 3/2009 |
| EP | 1653880 B1 | 4/2009 |
| EP | 2050474 A2 | 4/2009 |
| EP | 1940312 B1 | 7/2009 |
| FR | 2789888 | 8/2000 |
| FR | 2789888 A1 | 8/2000 |
| WO | WO8204390 A1 | 12/1982 |
| WO | WO92/06639 | 4/1992 |
| WO | WO9206639 A2 | 4/1992 |
| WO | WO9211824 A1 | 7/1992 |
| WO | WO9219162 A2 | 11/1992 |
| WO | WO9221293 A1 | 12/1992 |
| WO | WO9303685 A1 | 3/1993 |
| WO | WO9309722 A1 | 5/1993 |
| WO | WO9317635 A1 | 9/1993 |
| WO | WO9417747 A1 | 8/1994 |
| WO | WO9419029 A1 | 9/1994 |
| WO | WO94/27535 | 12/1994 |
| WO | WO9427535 A1 | 12/1994 |
| WO | WO9530374 A1 | 11/1995 |
| WO | WO9531140 A1 | 11/1995 |
| WO | WO9603091 A1 | 2/1996 |
| WO | WO9603165 A1 | 2/1996 |
| WO | WO9606634 A1 | 3/1996 |
| WO | WO9609795 A1 | 4/1996 |
| WO | WO9640307 A1 | 12/1996 |
| WO | WO9702789 A1 | 1/1997 |
| WO | WO9722371 A1 | 6/1997 |
| WO | WO9732526 A1 | 9/1997 |
| WO | WO9735533 A1 | 10/1997 |
| WO | WO9803713 A1 | 1/1998 |
| WO | WO98011814 | 3/1998 |

(56) References Cited

FOREIGN PATENT DOCUMENTS

| | | |
|---|---|---|
| WO | WO9814134 A2 | 4/1998 |
| WO | WO9816153 A1 | 4/1998 |
| WO | WO9903422 A1 | 1/1999 |
| WO | WO9905992 A1 | 2/1999 |
| WO | WO9916381 A1 | 4/1999 |
| WO | WO9951163 A1 | 10/1999 |
| WO | WO9960931 A1 | 12/1999 |
| WO | WO9962406 A2 | 12/1999 |
| WO | WO9963051 A2 | 12/1999 |
| WO | WO0007520 A1 | 2/2000 |
| WO | WO0016822 A2 | 3/2000 |
| WO | WO0056376 A1 | 9/2000 |
| WO | WO0057796 A1 | 10/2000 |
| WO | WO0057812 A1 | 10/2000 |
| WO | WO0061033 | 10/2000 |
| WO | WO0067663 A1 | 11/2000 |
| WO | WO0071548 A1 | 11/2000 |
| WO | WO0071549 A1 | 11/2000 |
| WO | WO0108594 A1 | 2/2001 |
| WO | WO0126588 A2 | 4/2001 |
| WO | WO0154589 A1 | 8/2001 |
| WO | WO0168653 A1 | 9/2001 |
| WO | WO0170322 A1 | 9/2001 |
| WO | WO0180788 A2 | 11/2001 |
| WO | WO0185058 A2 | 11/2001 |
| WO | WO0185060 | 11/2001 |
| WO | WO0189390 A1 | 11/2001 |
| WO | WO0189392 A2 | 11/2001 |
| WO | WO0207648 A1 | 1/2002 |
| WO | WO0217771 A2 | 3/2002 |
| WO | WO0217796 A1 | 3/2002 |
| WO | WO0217797 A1 | 3/2002 |
| WO | WO0219916 A1 | 3/2002 |
| WO | WO0219923 A1 | 3/2002 |
| WO | WO0222047 A1 | 3/2002 |
| WO | WO0224080 A2 | 3/2002 |
| WO | WO0226747 A1 | 4/2002 |
| WO | WO0230336 A2 | 4/2002 |
| WO | WO0232346 A1 | 4/2002 |
| WO | WO0234140 A2 | 5/2002 |
| WO | WO0235990 A2 | 5/2002 |
| WO | WO02058543 A2 | 8/2002 |
| WO | WO02078568 A1 | 10/2002 |
| WO | WO02080779 A1 | 10/2002 |
| WO | WO02080780 A1 | 10/2002 |
| WO | WO02/091953 | 11/2002 |
| WO | WO02087425 A2 | 11/2002 |
| WO | WO02091928 A1 | 11/2002 |
| WO | WO02091953 A1 | 11/2002 |
| WO | WO02096327 A2 | 12/2002 |
| WO | WO03002029 A1 | 1/2003 |
| WO | WO03002130 A1 | 1/2003 |
| WO | WO03032867 A1 | 4/2003 |
| WO | WO03059180 A2 | 7/2003 |
| WO | WO03059201 A1 | 7/2003 |
| WO | WO03059217 A1 | 7/2003 |
| WO | WO03077730 A2 | 9/2003 |
| WO | WO03082125 A1 | 10/2003 |
| WO | WO03084410 A1 | 10/2003 |
| WO | WO03088846 A1 | 10/2003 |
| WO | WO03090633 A2 | 11/2003 |
| WO | WO03092509 A1 | 11/2003 |
| WO | WO03094781 A1 | 11/2003 |
| WO | WO03094783 A1 | 11/2003 |
| WO | WO03094786 A1 | 11/2003 |
| WO | WO03094787 A1 | 11/2003 |
| WO | WO03096909 A1 | 11/2003 |
| WO | WO03096929 A1 | 11/2003 |
| WO | WO03097011 A1 | 11/2003 |
| WO | WO03099160 A1 | 12/2003 |
| WO | WO03103473 A2 | 12/2003 |
| WO | WO2004004600 A1 | 1/2004 |
| WO | WO2004006808 A2 | 1/2004 |
| WO | WO2004012579 A2 | 2/2004 |
| WO | WO2004012627 A1 | 2/2004 |
| WO | WO2004019787 A2 | 3/2004 |
| WO | WO2004024030 A1 | 3/2004 |
| WO | WO2004034924 A2 | 4/2004 |
| WO | WO2004037123 A1 | 5/2004 |
| WO | WO2004/062529 | 7/2004 |
| WO | WO2004058286 A1 | 7/2004 |
| WO | WO2004060425 A2 | 7/2004 |
| WO | WO2004062529 A2 | 7/2004 |
| WO | WO2004062530 A1 | 7/2004 |
| WO | WO2004028547 A1 | 8/2004 |
| WO | WO2004069866 A1 | 8/2004 |
| WO | WO2004/080348 | 9/2004 |
| WO | WO2004080348 A1 | 9/2004 |
| WO | WO2004087227 A1 | 10/2004 |
| WO | WO2004093737 A1 | 11/2004 |
| WO | WO2004098461 A2 | 11/2004 |
| WO | WO2004098665 A1 | 11/2004 |
| WO | WO2004100841 A1 | 11/2004 |
| WO | WO2004101002 A2 | 11/2004 |
| WO | WO2004103166 A2 | 12/2004 |
| WO | WO2004103414 A2 | 12/2004 |
| WO | WO2005003351 A1 | 1/2005 |
| WO | WO2005004727 A1 | 1/2005 |
| WO | WO2005007209 A1 | 1/2005 |
| WO | WO2005014634 A2 | 2/2005 |
| WO | WO2005018494 A1 | 3/2005 |
| WO | WO2005019241 A2 | 3/2005 |
| WO | WO2005019315 A1 | 3/2005 |
| WO | WO2005035548 A1 | 4/2005 |
| WO | WO2005041784 A2 | 5/2005 |
| WO | WO2005044143 A1 | 5/2005 |
| WO | WO2005051172 A2 | 6/2005 |
| WO | WO2005055958 A2 | 6/2005 |
| WO | WO2005065324 A2 | 7/2005 |
| WO | WO2005065552 A2 | 7/2005 |
| WO | WO2005079335 A2 | 9/2005 |
| WO | WO2005082274 A1 | 9/2005 |
| WO | WO2005094721 A1 | 10/2005 |
| WO | WO2005099628 A2 | 10/2005 |
| WO | WO2005102209 A1 | 11/2005 |
| WO | WO2005105172 A1 | 11/2005 |
| WO | WO2005110243 A2 | 11/2005 |
| WO | WO2005110273 A1 | 11/2005 |
| WO | WO2006002439 A1 | 1/2006 |
| WO | WO2006008429 A1 | 1/2006 |
| WO | WO2006012353 A2 | 2/2006 |
| WO | WO2006013337 A2 | 2/2006 |
| WO | WO2006015031 A2 | 2/2006 |
| WO | WO2006026509 A2 | 3/2006 |
| WO | WO2006034117 A1 | 3/2006 |
| WO | WO2006036936 A2 | 4/2006 |
| WO | WO2006037047 A2 | 4/2006 |
| WO | WO2006040760 A1 | 4/2006 |
| WO | WO2006044785 A1 | 4/2006 |
| WO | WO2006047645 A2 | 5/2006 |
| WO | WO2006048885 A1 | 5/2006 |
| WO | WO2006082587 A2 | 8/2006 |
| WO | WO2006086339 A2 | 8/2006 |
| WO | WO2006092159 A1 | 9/2006 |
| WO | WO2006092236 A1 | 9/2006 |
| WO | WO2006102457 A2 | 9/2006 |
| WO | WO2006116000 A2 | 11/2006 |
| WO | WO2006119034 A2 | 11/2006 |
| WO | WO2007004228 A1 | 1/2007 |
| WO | WO2007011689 A2 | 1/2007 |
| WO | WO2007017872 A2 | 2/2007 |
| WO | WO2007021620 A2 | 2/2007 |
| WO | WO2007021759 A2 | 2/2007 |
| WO | WO2007021834 A1 | 2/2007 |
| WO | WO2007/025302 | 3/2007 |
| WO | WO/2007/030676 | 3/2007 |
| WO | WO2007025293 A2 | 3/2007 |
| WO | WO2007025296 A2 | 3/2007 |
| WO | WO2007025302 A2 | 3/2007 |
| WO | WO2007030676 A2 | 3/2007 |
| WO | WO2007034145 A2 | 3/2007 |
| WO | WO2007050382 A1 | 5/2007 |
| WO | WO2007051221 A1 | 5/2007 |
| WO | WO2007055755 A1 | 5/2007 |

(56) References Cited

FOREIGN PATENT DOCUMENTS

| | | |
|---|---|---|
| WO | WO2007070141 A1 | 6/2007 |
| WO | WO2007072469 A2 | 6/2007 |
| WO | WO2007081955 A1 | 7/2007 |
| WO | WO2007087132 A1 | 8/2007 |
| WO | WO2007087146 A2 | 8/2007 |
| WO | WO2007115110 A2 | 10/2007 |
| WO | WO2007129220 A2 | 11/2007 |
| WO | WO2007133311 A2 | 11/2007 |
| WO | WO2007136820 A2 | 11/2007 |
| WO | WO2007137211 A2 | 11/2007 |
| WO | WO2007143726 A2 | 12/2007 |
| WO | WO2007144782 A2 | 12/2007 |
| WO | WO2007146784 A2 | 12/2007 |
| WO | WO2008006097 A2 | 1/2008 |
| WO | WO2008016802 A1 | 2/2008 |
| WO | WO2008026905 A2 | 3/2008 |
| WO | WO2008030873 A2 | 3/2008 |
| WO | WO2008030939 A2 | 3/2008 |
| WO | WO2008/045635 | 4/2008 |
| WO | WO2008045635 A2 | 4/2008 |
| WO | WO2008055028 A1 | 5/2008 |
| WO | WO2008/065653 | 6/2008 |
| WO | WO2008065653 A1 | 6/2008 |
| WO | WO2008069919 A2 | 6/2008 |
| WO | WO2008083484 A1 | 7/2008 |
| WO | WO2008085825 A1 | 7/2008 |
| WO | WO2008/099382 | 8/2008 |
| WO | WO2008094217 A1 | 8/2008 |
| WO | WO2008094842 A1 | 8/2008 |
| WO | WO2008099382 A1 | 8/2008 |
| WO | WO2008112437 A2 | 9/2008 |
| WO | WO2008124056 A1 | 10/2008 |
| WO | WO2008140989 A2 | 11/2008 |
| WO | WO2008157497 A2 | 12/2008 |
| WO | WO2008157777 A1 | 12/2008 |
| WO | WO2009005625 A1 | 1/2009 |
| WO | WO2009005634 A1 | 1/2009 |
| WO | WO2009011824 A1 | 1/2009 |
| WO | WO2009012001 A1 | 1/2009 |
| WO | WO2009022348 A1 | 2/2009 |
| WO | WO2009036094 A2 | 3/2009 |
| WO | WO2009039371 A1 | 3/2009 |
| WO | WO2009/050717 | 4/2009 |
| WO | WO2009042442 A1 | 4/2009 |
| WO | WO2009048314 A1 | 4/2009 |
| WO | WO2009050717 A2 | 4/2009 |
| WO | WO2009059005 A1 | 5/2009 |
| WO | WO2009064845 A2 | 5/2009 |
| WO | WO2009069119 A1 | 6/2009 |
| WO | WO2009075786 A1 | 6/2009 |
| WO | WO2009075932 A1 | 6/2009 |
| WO | WO2009075933 A1 | 6/2009 |
| WO | WO2009086446 A1 | 7/2009 |
| WO | WO2009092294 A1 | 7/2009 |
| WO | WO2009094015 A1 | 7/2009 |
| WO | WO2009/104182 | 8/2009 |
| WO | WO2009097380 A1 | 8/2009 |
| WO | WO2009102792 A2 | 8/2009 |
| WO | WO2009104182 A2 | 8/2009 |
| WO | WO2009113972 A2 | 9/2009 |
| WO | WO2009126781 A1 | 10/2009 |
| WO | 2011/021082 A1 | 2/2011 |

\* cited by examiner

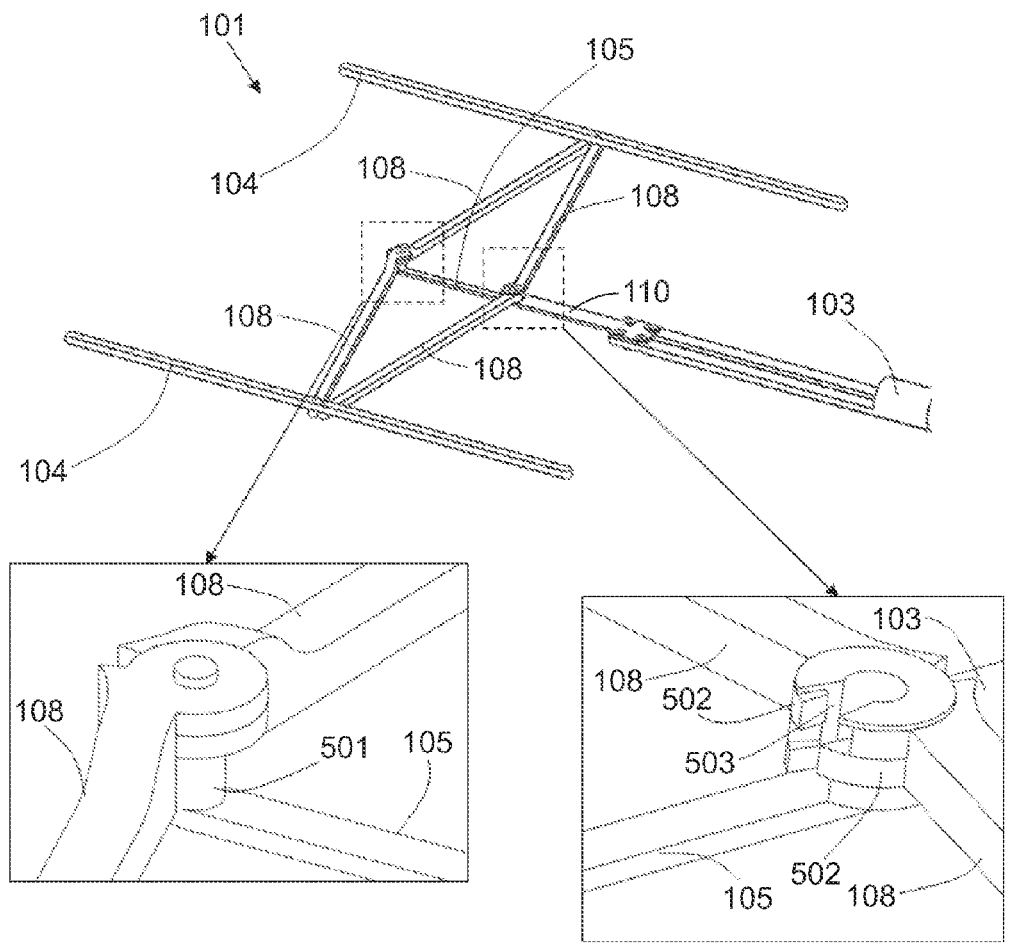
FIG. 9A1

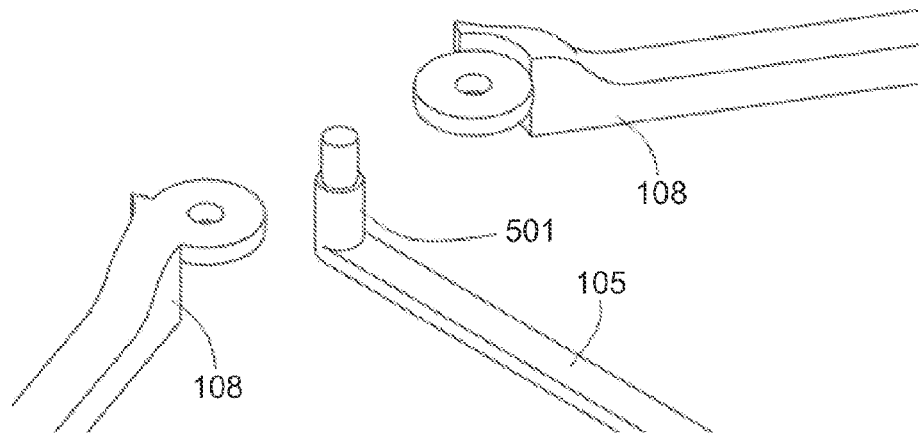
FIG. 9A2
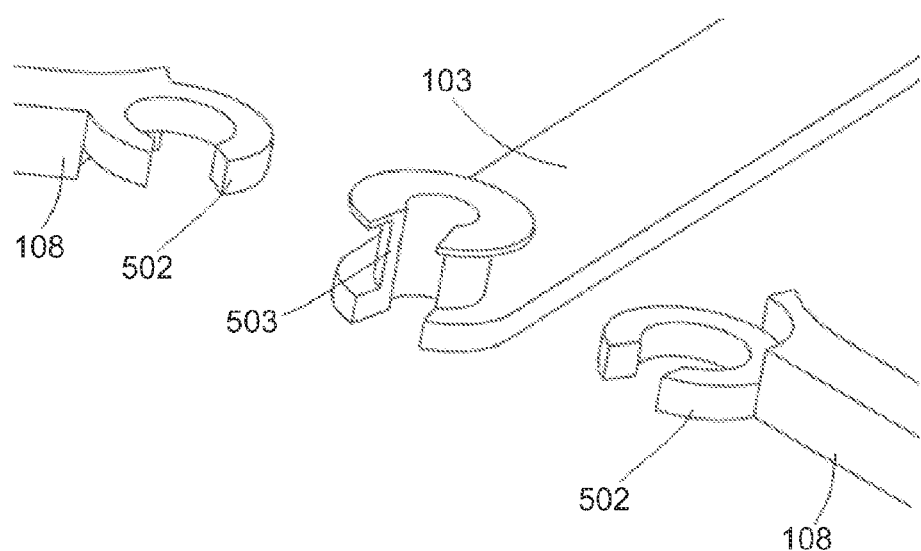
FIG. 9A3

PRIOR ART

ARTICULATING PATCH DEPLOYMENT DEVICE AND METHOD OF USE

RELATED APPLICATION

The present application claims the benefit of and priority to U.S. provisional patent application Ser. No. 61/234,320, filed Aug. 17, 2009, the content of which is incorporated by reference herein in its entirety.

FIELD OF THE INVENTION

The invention generally relates to devices and methods for repairing an aperture in biological tissue. In certain embodiments, the invention provides devices and methods for deploying an implant to interact with biological tissue during a surgery.

BACKGROUND OF THE INVENTION

An object of the present invention is to provide apparatus and a method for performing corrective surgery on internal wounds such as hernia where invasion of the patient's body tissues is minimized and the resultant trauma is reduced.

A hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the patch and then to attach the patch to the tissue.

There are a few patent and patent applications teaching the deployment of patches. For example U.S. Pat. No. 5,836,961 (refers hereinafter as '961) which relates to an apparatus used for developing an anatomic space for laparoscopic hernia repair and a patch for use therewith. The apparatus of patent '961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

Although patent '961 relates to deploying means, patent '961 teaches a device in which the patch is attached to a balloon which is introduced into the abdominal cavity; patent '961 does not disclose means for enabling flexibility of the system to better fit itself to the landscape of the tissue. In other words, there is no disclosure of means of articulating so as to provide better compatibility of the deployment system and the tissue.

Another example for deploying the patch can be found in U.S. Pat. No. 5,370,650 (refers hereinafter as '650) which relates to an apparatus for positioning surgical implants adjacent to body tissue to facilitate the fastening of the implant to the body tissue. Patent '650 provides an apparatus for positioning surgical implants adjacent to body tissue, comprising an outer tube having a proximal end, a distal end and a longitudinal axis; an inner rod at least partially disposed within the outer tube and slidable along said longitudinal axis. The inner rod has a proximal and a distal end portions.

The inner rod distal end portion further comprises articulating means for pivoting at an angle with respect to the longitudinal axis (a preferred embodiment illustrating the teaching of patent '650 is illustrated in FIG. 11). The articulation is provided by a spring-like flexible rod 18 encapsulated within rigid tube 12. By pulling tube 12, the flexible rod 18 bends and hence provide articulation.

More patent literature can be found in PCT no. WO08065653 (refers hereinafter as '653) relates to a device especially adapted to deploy a patch within a body cavity. The device is an elongate open-bored applicator (EOBP) and comprises (a) at least one inflatable contour-balloon, (b) at least one inflatable dissection balloon. The inflatable contour-balloon and the inflatable dissection balloon are adjustable and located at the distal portion. The EOBP additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

It should be pointed out that PCT '653 does not disclose nor claim articulation means.

Articulation is highly important since it enables the optimum positioning and orientation of the patch relatively to the hernia. Such optimum positioning and orientation is provided no matter what is the entrance angle of the patch to the abdominal cavity.

None of the patent literatures found to teach articulating means for providing optimal positioning and orientation of the patch relatively to the tissue.

Hence there is still a long felt need for a patch deployment mechanism enabling such articulation.

SUMMARY OF THE INVENTION

It is one onject of the present invention to provide an articulating lateral deployment device (ALDD) adapted to both deploy a patch within the abdominal cavity in a bidirectional and controlled manner and to enable vertically and laterally articulation such that said patch is oriented within said cavity.

It is another object of the present invention to provide the articulating lateral deployment device (ALDD) as defined above, wherein said ALDD is characterized by having a distal portion 101, adapted to be inserted into a body and a proximal portion 102, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end of said tube; said central shaft (105) is adapted to reciprocally move within said tube (103); said movement is parallel to said main longitudinal axis; said distal portion comprises:
  (i) at least two frame arms (FA) (104) adapted to be reversibly coupled to said patch;
  (ii) at least two proximal deployment arms (pDA) (108*a*, 108*b*) hinge-like connected to said TD and to the proximal end of said two FA;
  (iii) at least two distal deployment arms (dDA) (108*c*, 108*d*) hinge-like connected to said CSD and to the distal end of said two FA; each of said pDA and dDA (108*a*, 108*b*, 108*c*, 108*d*) is characterized by a plurality of configurations, at least one of said configurations is a parallel configuration in which each of said pDA and dDA is substantially parallel to said central shaft (105); and, at least one of said configurations is a substantially perpendicular configuration in which each of said pDA and dDA is substantially perpendicular to said central shaft (105); said FA (104) are characterized by a closed configuration; and, an open configuration at which said patch is deployed; said FA are adapted to reversibly transform from said closed configuration to said open configuration by (i) said reciprocal movement of said central shaft (105) towards and away from said proximal portion; and, (ii) said transformation of each of said DAs from said parallel configuration to said perpendicular configuration, such that said deployment of said patch is at least partially reversible;
  (iv) a lateral articulating mechanism (1000) for providing lateral articulation to said ALDD; and,
  (v) vertical articulating mechanism (2000) for providing vertical articulation to said ALDD;
  said proximal portion comprising at least one handle (102) located outside said body; said handle is adapted to (i) reversibly transform said FA from said closed configuration to said open configuration; (ii) lateral articulate said ALDD.

It is another object of the present invention to provide the articulating lateral deployment device (ALDD) as defined above, wherein said lateral articulating mechanism (1000) comprises (i) two wedge-like segments (1001, 1002) coupled together via a hinge connection (201); at least one of said segments is coupled to said TD and at least one of said segments is coupled to said at least two pDA; (ii) at least two articulation wires (202) threaded through said two wedge-like segments (1001, 1002); each of which is coupled to one of said pDA; such that said lateral articulation is provided by the application of pulling forces on one of said wires.

It is another object of the present invention to provide the articulating lateral deployment device (ALDD) as defined above, wherein said hinge-like connection are selected from a group consisting of hinge-like connection, living hinge connection or any combination thereof.

It is another object of the present invention to provide the articulating lateral deployment device (ALDD) as defined above, wherein said vertical articulating mechanism (2000) comprises hinge connection (203) between said tube (103) and said distal portion (101); such that said vertical articulation is provided by application of pressing forces on said ALDD against a hernia defect.

It is another object of the present invention to provide the articulating lateral deployment device (ALDD) as defined above, wherein said FA (104) comprises means adapted to at least partially reversibly connect said patch (106) to said FA (104).

It is another object of the present invention to provide the articulating lateral deployment device (ALDD) as defined above, wherein said FA (104) comprises means adapted to at least partially connect said patch (106) to said tissue.

It is another object of the present invention to provide the articulating lateral deployment device (ALDD) as defined above, wherein said means are selected from a group consisting of biological glue, clips, tacks or any combination thereof.

It is another object of the present invention to provide the articulating lateral deployment device (ALDD) as defined above, wherein said central shaft is composed of a single homogeneous and continuous segment.

It is another object of the present invention to provide the articulating lateral deployment device (ALDD) as defined above, wherein said central shaft is composed of at least one proximal segment (CSP) (105*b*) and at least one distal segment (CSD) (105*a*).

It is another object of the present invention to provide the articulating lateral deployment device (ALDD) as defined above, wherein said two segments are connected via a flexibility region (301).

It is another object of the present invention to provide the articulating lateral deployment device (ALDD) as defined above, wherein said central shaft is characterized by at least one open state in which said proximal segment and said distal segment are coupled together via at least one pin (304) such that at least a portion of said central shaft is flexible; and a closed configuration in which said proximal segment and said distal segment are in physical contact and are coupled together via at least two pins (304, 306) such that said central shaft is rigid.

It is another object of the present invention to provide the articulating lateral deployment device (ALDD) as defined above, wherein said CSD comprises an elongated sleeve (308) adapted to envelope said CSP.

It is another object of the present invention to provide the articulating lateral deployment device (ALDD) as defined above, wherein said central shaft is characterized by at least one flexible configuration in which said central shaft is flexible; and a rigid configuration in which said central shaft is rigid.

It is another object of the present invention to provide the articulating lateral deployment device (ALDD) as defined above, wherein said central shaft is transformed from said rigid configuration to said flexible configuration and from said flexible configuration to said rigid configuration by said reciprocal movement of said CSP with regards to said CSD.

It is another object of the present invention to provide the articulating lateral deployment device (ALDD) as defined above, wherein said lateral articulation is provided by connection selected from a group consisting of hinge-like connection, living hinge connection or any combination thereof between said two dDAs and between said two pDAs.

It is another object of the present invention to provide the articulating lateral deployment device (ALDD) as defined above, wherein each of said FAs are pre-shaped so as to better extract said FAs in said closed configuration of said cavity.

It is another object of the present invention to provide the articulating lateral deployment device (ALDD) as defined above, wherein said pre-shaped FAs are bended with respect to said central shaft.

It is another object of the present invention to provide the articulating lateral deployment device (ALDD) as defined above, wherein said ALDD additionally comprising a flexible wire 1501 coupled to said distal end of said tube 103; said flexible wire 1501 is adapted to encircle the proximal portion of said FAs.

It is another object of the present invention to a method for deploying a patch within the abdominal cavity. The method comprises steps selected inter alia form:
  a. providing an articulating lateral deployment device (ALDD) characterized by having a distal portion 101, adapted to be inserted into a body and a proximal portion 102, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end of said tube; said central shaft (105) is adapted to reciprocally move within said tube (103); said movement is parallel to said main longitudinal axis; said distal portion comprises:
    (i) at least two frame arms (FA) (104) adapted to be reversibly coupled to said patch;
    (ii) at least two proximal deployment arms (pDA) (108a, 108b) hinge-like connected to said TD and to the proximal end of said two FA;
    (iii) at least two distal deployment arms (dDA) (108c, 108d) hinge-like connected to said CSD and to the distal end of said two FA; each of said pDA and dDA (108a, 108b, 108c, 108d) is characterized by a plurality of configurations, at least one of said configurations is a parallel configuration in which each of said pDA and dDA is substantially parallel to said central shaft (105); and, at least one of said configurations is a substantially perpendicular configuration in which each of said pDA and dDA is substantially perpendicular to said central shaft (105); said FA (104) are characterized by a closed configuration; and, an open configuration at which said patch is deployed; said FA are adapted to reversibly transform from said closed configuration to said open configuration by (i) said reciprocal movement of said central shaft (105) towards and away from said proximal portion; and, (ii) said transformation of each of said DAs from said parallel configuration to said perpendicular configuration, such that said deployment of said patch is at least partially reversible;
    (iv) a lateral articulating mechanism (1000) for providing lateral articulation to said ALDD; and,
    (v) vertical articulating mechanism (2000) for providing vertical articulation to said ALDD;
    said proximal portion comprising at least one handle (102) located outside said body; said handle is adapted to (i) reversibly transform said FA from said closed configuration to said open configuration; (ii) lateral articulate said ALDD;
  b. reversibly attaching said patch to said FAs;
  c. adjusting said patch on said FAs;
  d. introducing said distal portion into said body cavity;
  e. reversibly transforming said FA from said closed configuration to said open configuration; thereby deploying said patch;
  f. laterally articulating said ALDD so as said patch is orientated with respect to the treated defect;
  g. adjacently bringing said patch into contact with the biological tissue containing the defect; by vertically articulating said ALDD;
  h. attaching said patch to said biological tissue;
  i. detaching said patch from said FA;
  j. transforming said FA from said open configuration to said closed configuration; and,
  k. extracting said ALDD from said body cavity.

It is another object of the present invention to provide the method as defined above, additionally comprising step of composing said central shaft of a single homogeneous and continuous segment.

It is another object of the present invention to provide the method as defined above, additionally comprising step of composing said central shaft of at least one proximal segment (105b) and at least one distal segment (105a).

It is another object of the present invention to provide the method as defined above, additionally comprising step of coupling said two segments via a flexibility region (301).

It is another object of the present invention to provide the method as defined above, wherein said step of reversibly transforming said FA from said closed configuration to said open configuration provides a controlled continuous deployment of said patch.

It is another object of the present invention to provide the method as defined above, wherein said step of reversibly transforming said FA from said closed configuration to said open configuration provides a bidirectional fully reversible deployment.

It is another object of the present invention to provide the method as defined above, wherein said step of reversibly transforming said FA from said closed configuration to said open configuration is performed by transforming said pDAs and said dDAs from said parallel configuration to said perpendicular configuration.

It is another object of the present invention to provide the method as defined above, additionally comprising a second step of attaching said patch to said biological tissue is performed using conventional attaching means.

It is another object of the present invention to provide the method as defined above, additionally comprising step of laterally rotating said patch with respect to said tissue, such that the right orientation of said patch is obtained.

It is another object of the present invention to provide the method as defined above, additionally comprising step of verifying correct location of said patch 106 with regards to said defect, further wherein said step of verifying is perform prior to said step of attaching said patch to said biological tissue.

It is another object of the present invention to provide the articulating lateral deployment device (ALDD) as defined above, wherein said ALDD is characterized by having a distal portion 101, adapted to be inserted into a body and a proximal portion 102, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end of said tube;

said distal portion comprises:
- (i) a deployment cart (601) adapted to reciprocally slide along at least a portion of said central shaft (105);
- (ii) at least two proximal deployment arms (pDA) (108a, 108b) hinge-like connected to said TD and to the proximal end of said two FA;
- (iii) at least two distal deployment arms (dDA) (108c, 108d) hinge-like connected to said deployment cart (601) and to the distal end of said two FA;
  - each of said pDA and dDA (108a, 108b, 108c, 108d) is characterized by a plurality of configurations, at least one of said configurations is a parallel configuration in which each of said pDA and dDA is substantially parallel to said central shaft (105); and, at least one of said configurations is a substantially perpendicular configuration in which each of said pDA and dDA is substantially perpendicular to said central shaft (105);
  - said FA (104) are characterized by a closed configuration; and, an open configuration at which said patch is deployed; said FA are adapted to reversibly transform from said closed configuration to said open configuration by (i) said reciprocal movement of said cart (601) towards and away from said proximal portion; and, (ii) said transformation of each of said DAs from said parallel configuration to said perpendicular configuration, such that said deployment of said patch is at least partially reversible
- (iv) deployment cart(iii) at least two frame arms (FA) (104), each of which is coupled to at least two of said DAs (108a, 108b, 108c, 108d), adapted to be reversibly coupled to said patch;

said deployment cart 601 is adapted to reciprocally slide along at least a portion of said central shaft (105); said movement is parallel to said main longitudinal axis;

said FAs (104) are characterized by a closed configuration; and, an open configuration at which said patch is deployed; said FAs are adapted to reversibly transform from said closed configuration to said open configuration by (i) said reciprocal movement of said deployment cart (601) towards and away from said proximal portion; and, (ii) said transformation of each of said DA from said parallel configuration to said perpendicular configuration, such that said deployment of said patch is at least partially reversible;

said proximal portion comprising at least one handle (102) located outside said body; said handle is adapted to (i) reversibly transform said FA from said IS to said FS; (ii) lateral articulate said ALDD;

said TD is mechanically coupled to (i) a lateral articulating mechanism (1000) for providing lateral articulation to said ALDD; and, (ii) vertical articulating mechanism (2000) for providing vertical articulation to said ALDD.

It is another object of the present invention to provide the articulating lateral deployment device (ALDD) as defined above, wherein said hinge-like connection are selected from a group consisting of hinge-like connection, living hinge-like connection or any combination thereof.

It is another object of the present invention to provide the articulating lateral deployment device (ALDD) as defined above, additionally comprising an elongated deployment wire 602 coupled to said deployment cart 601; said deployment wire 602 is adapted to reciprocally move said deployment cart 601.

It is another object of the present invention to provide the articulating lateral deployment device (ALDD) as defined above, wherein said lateral articulating mechanism (1000) comprises (i) two wedge-like segments 1001 and 1002 coupled together via a hinge connection (201); (ii) at least two articulation wires (202) threaded through said two wedge-like segments (1001, 1002) and are connecting said distal portion (101) to said proximal portion (102); such that said lateral articulation is provided by application of pulling forces on one of said wires.

It is another object of the present invention to provide the articulating lateral deployment device (ALDD) as defined above, wherein said vertical articulating mechanism (2000) comprises hinge connection (203) between said tube (103) and said distal portion (101); such that said vertical articulation is provided by application of pressing forces on said ALDD against a defect.

It is another object of the present invention to provide the articulating lateral deployment device (ALDD) as defined above, wherein said FA (104) comprises (a) means adapted to attach said patch to a defect; and, (b) means adapted to at least partially reversibly connect said patch (106) to said FA (104).

It is another object of the present invention to provide the articulating lateral deployment device (ALDD) as defined above, wherein said central shaft is composed of a single homogeneous and continuous segment.

It is another object of the present invention to provide the articulating lateral deployment device (ALDD) as defined above, wherein said central shaft is composed of at least one proximal segment (CSP) (105b) and at least one distal segment (CSD) (105a).

It is another object of the present invention to provide the articulating lateral deployment device (ALDD) as defined above, wherein said two segments are connected via a flexibility region (301).

It is another object of the present invention to provide the articulating lateral deployment device (ALDD) as defined above, wherein said central shaft is characterized by at least one open state in which said proximal segment and said distal segment are coupled together via at least one pine (304) such that at least a portion of said central shaft is flexible; and a closed configuration in which said proximal segment and said distal segment are in physical contact and are coupled together via at least two pins (304, 306) such that said central shaft is rigid.

It is another object of the present invention to provide the articulating lateral deployment device (ALDD) as defined above, wherein said CSD comprises an elongated sleeve (308) adapted to envelope said CSP.

It is another object of the present invention to provide the articulating lateral deployment device (ALDD) as defined above, wherein each of said FAs are pre-shaped so as to better extract said FAs in said closed configuration of said cavity.

It is another object of the present invention to provide the articulating lateral deployment device (ALDD) as defined above, wherein said pre-shaped FAs are bended with respect to said central shaft.

It is another object of the present invention to provide the articulating lateral deployment device (ALDD) as defined above, wherein said ALDD additionally comprising a flexible wire 1501 coupled to said distal end of said tube 103; said flexible wire 1501 is adapted to encircle the proximal portion of said FAs.

It is another object of the present invention to provide the articulating lateral deployment device (ALDD) as defined above, wherein said FA (104) comprises means adapted to at least partially reversibly connect said patch (106) to said FA (104).

It is another object of the present invention to provide the articulating lateral deployment device (ALDD) as defined above, wherein said FA (104) comprises means adapted to at least partially connect said patch (106) to said tissue.

It is another object of the present invention to provide the articulating lateral deployment device (ALDD) as defined above, wherein said means are selected from a group consisting of biological glue, clips, tackers or any combination thereof.

It is still an object of the present invention to provide the articulating lateral deployment device (ALDD) as defined above, wherein said central shaft is characterized by at least one flexible configuration in which said central shaft is flexible; and a rigid configuration in which said central shaft is rigid.

It is lastly an object of the present invention to provide the articulating lateral deployment device (ALDD) as defined above, wherein said central shaft is transformed from said rigid configuration to said flexible configuration and from said flexible configuration to said rigid configuration by said reciprocal movement of said CSP with regards to said CSD.

BRIEF DESCRIPTION OF THE DRAWINGS

The invention is herein described, by way of example only, with reference to the accompanying drawings, wherein:

FIGS. 9A-9D illustrate another embodiment of the lateral articulating mechanism (3000).

DETAIL DESCRIPTION OF THE SPECIFIC EMBODIMENTS

Figure 1A:
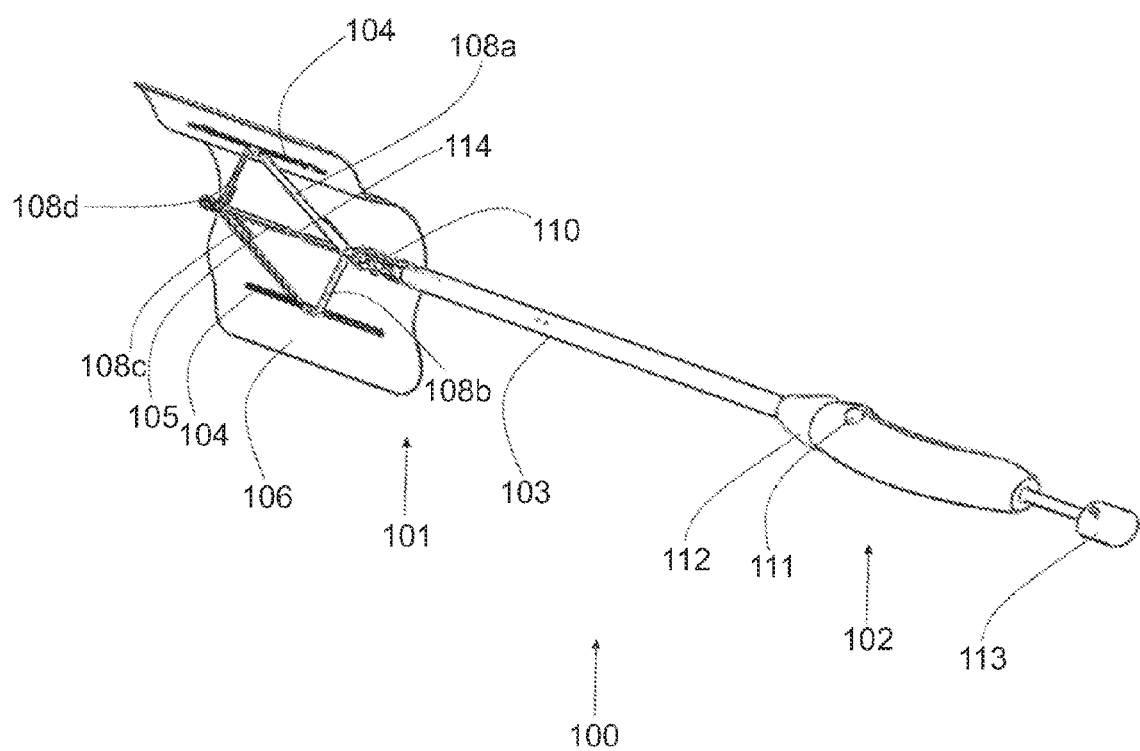
FIG. 1A illustrating an embodiment of the present invention.

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides a device and method for deploying and a patch and optimally positioning said patch with respect to the hernia.

The present invention provides an articulating lateral deployment device (ALDD) wherein the ALDD is adapted to actively deploy and place a prostatic patch during surgery while providing articulation in order to allow proper location and orientation of the patch with respect to the treated tissue defect. The present invention also provides a method for deploying and attaching a patch to a biological tissue during surgery utilizing the ALDD device.

It should be emphasized that some of the major advantages of the present invention, with respect to the prior art, is to provide a deployment system or a deployment and attachment system that enables (a) an actively deployment—the deployment is actively controlled by the surgeon (as opposed to passive deployment); and (b) the deployment is continuous (analogous and not binary such that several deployment levels can be obtained);

The term "Hernia" refers hereinafter to umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components. The term "hinge like connection" can refer to a standard hinge or to a living hinge (i.e., a thin flexible hinge (flexure bearing) made from plastic that joins two rigid parts together while allowing them to bend along the line of the hinge).

The term 'controlled deployment' refers hereinafter to a patch deployment which is continuous; i.e., the deployment is not binary but analogous—there are several deployment levels. This is in contrast so conventional deployment system is now days (see for example U.S. Pat. No. 5,370,650, FIG. 17), in which the deployment of the patch relies upon the elasticity of a loop member surrounding the patch such that the patch can be either fully folded or fully unfolded. No intermediate are enabled. In the present invention there can be several deployment stages.

The term 'bidirectional' or 'fully reversible deployment' refers hereinafter to the deployment of the patch, which according to the present invention, is fully reversible. In other words, the patch deployment is bidirectional, i.e., the patch can be fully folded (i.e., deployed within the body) and then, if the surgeon desires, the patch can be fully unfolded simply by the reconfiguration of the flexible arms from the initial stage to the final stage and vice versa.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh/patch within the abdominal cavity so as to fit to the hernia. Usually the mesh/patch is elongated (i.e., rectangular or i.e., ellipse)—therefore it has different directions. By rotating the mesh within the abdominal cavity—one can decide which direction is turned where.

The term "adjusting" refers hereinafter to rolling, folding and winding of the patch, thus preparing and enabling the insertion of said patch into the abdominal cavity.

Before explaining the figures, it should be understood that the invention is not limited in its application to the details of construction and the arrangement of the components set forth in the following description or illustrated in the drawings. The invention can be carried out in various ways.

Reference is now made to FIG. 1A illustrating an embodiment of the present invention. According to that embodiment an articulating lateral deployment device (ALDD) which is adapted for deployment and placement of a prosthetic patch during a minimal invasive (i.e., Laparoscopic) hernia repair surgery is provided.

The ALDD 100 comprises of 2 main portions: distal portion 101, and a proximal portion 102. The two portions are connected via a tube 103. The distal portion is adapted to be inserted into a body during the surgery via a trocar. The distal portion is also adapted to deploy and place a prosthetic hernia repair patch 106 onto the patient's tissue surface.

The distal portion comprises of at least two frame arms (FA) 104, at least 4 deployment arms (DA) 108 and a central shaft 105 adapted to reciprocally move within tube 103.

The DAs 108 can be divided into two groups: 2 DAs (108a and 108b) which are proximally located and 2 DAs (108d and 108c) which are distally located.

The proximal DAs 108a and 108b are connected at their proximal end to tube 103's distal end and at their distal end to the FA 104. The distal DAs 108c and 108d are connected at their distal end to the central shaft 105 and at their proximal end to the FAs 104. All said connections are hinge connections.

Each of said DAs (108) is characterized by a plurality of configurations. One of said configuration is a parallel configuration in which the DAs are substantially parallel to said central shaft (105); another one of said configuration is a substantially perpendicular configuration in which said DAs are substantially perpendicular to said central shaft (105).

At the rest of said configurations, the DAs are positioned at an angle A with respect to said central shaft (105). Angle A can be at a range of about 0 degrees to about 180 degrees.

The patch/mesh/net 106 is reversibly attached to the FAs 104 by a patch attachment means (PAM) 107 (not shown in the figure).

The distal portion 101 is adapted to be rotated laterally (i.e. left and right with regards to tube 103) and vertically (i.e. up and down in relation to the tube 103), such that the patch could be properly aligned and oriented within the abdominal cavity with regards to the hernia. Such rotation is enabled via the articulating means as will be described hereinafter. The proximal portion 102 comprises (a) a deployment lever 113 which provides the surgeon the ability to control the deployment process; (b) an articulation lever 112 which provides the surgeon the ability to control lateral articulation angle of the distal portion; and, (c) a release button 111 which provides the surgeon the ability to roll the distal portion to its close configuration prior to its extraction for the patient's body.

Figure 1B:
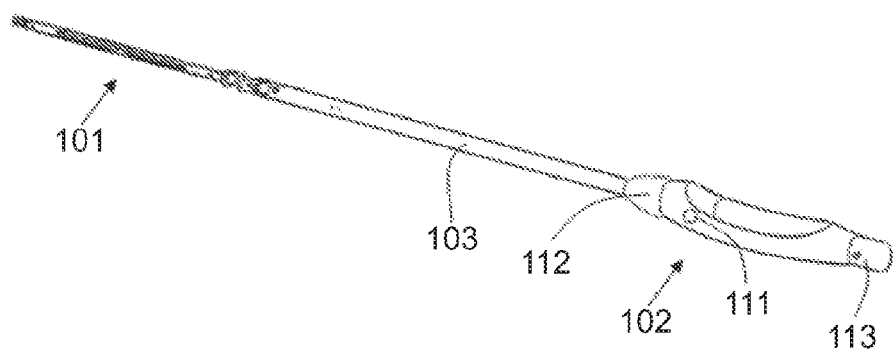
FIGS. 1B-1C illustrate the deployment mechanism of device 100.
Figure 1C:
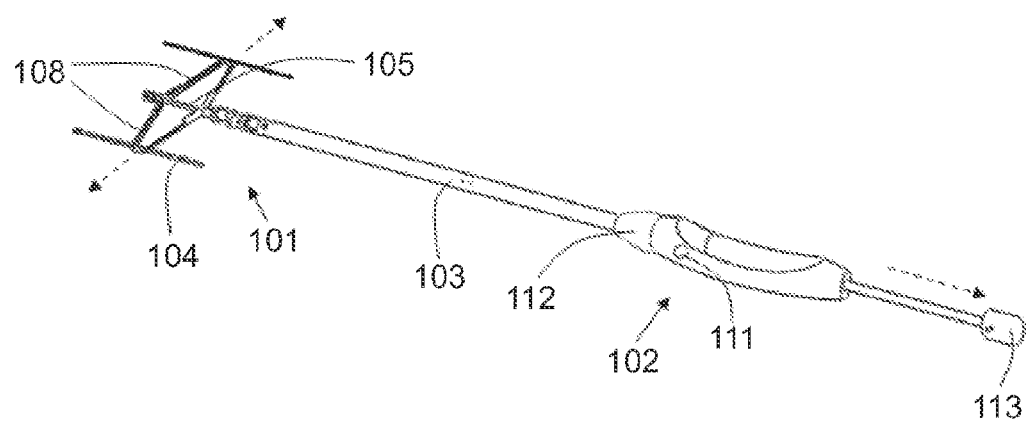

Reference is now made to FIGS. 1B-1C which illustrate the deployment mechanism of device 100. The close configuration is described in FIG. 1B while the deployed configuration is describe in FIG. 1C.

One the system is in its closed configuration, the distal portion cross section area is less than the inner cross section area of the trocar such that patch 106 can be rolled onto the distal portion and inserted into the patient's abdominal cavity via said trocar.

As can be seen in FIG. 1C, once the device is inserted to the patient's abdominal cavity, the patch 106 is deployed by reciprocal movement of the central shaft 105 toward the proximal portion 102. The deployment is activated by the deployment lever 113.

The deployment of the patch is as follows: By linearly pulling the deployment lever 113 toward the proximal portion 102, the central shaft 105 is proximally pulled. Since the DAs are coupled to the central shaft 105, the DAs 108 will laterally open (i.e., away from the central shaft 105), and will be transformed from their parallel configuration to their perpendicular configuration. Since they are coupled to the FA's they will push the FAs 104 away from each other, and hence, will spread the patch 106.

Figure 2A:
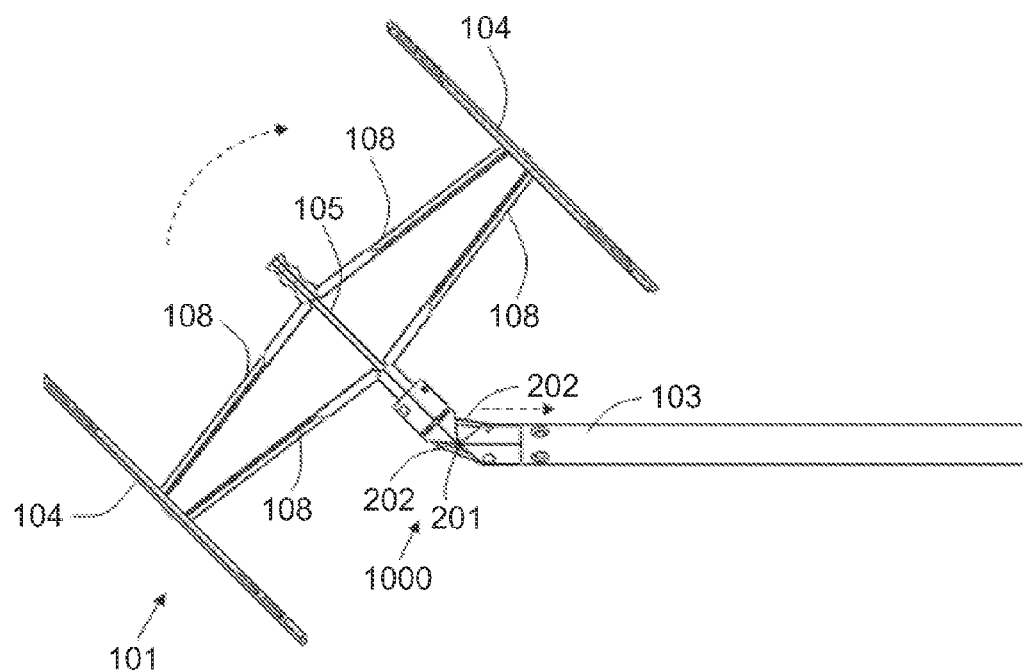
FIGS. 2A-2B illustrating one embodiment of the lateral articulation mechanism 1000.
Figure 2B:
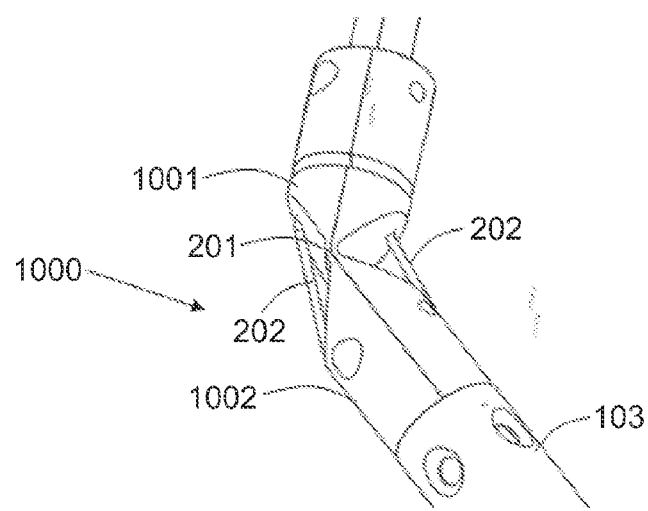

Reference is now being made to FIGS. 2A-2B illustrating one embodiment of the lateral articulation mechanism 1000. According to this embodiment, the lateral articulation mechanism 1000 functions as a hinge between tube 103 and the distal portion 101.

The articulation mechanism 1000 comprises two wedge-like segments 1001 and 1002 coupled together via a lateral hinge connection 201.

Two articulation wires 202 threaded through said two wedge-like segments 1001 and 1002 and are connected between the proximal portion 102 and (through tube 103). the distal portion 101 through the tube 103.

When one of said wires is pulled, the tension in said wire is increased relatively to the other wire and a lateral rotation moment is applied to the hinge 201. This moment rotates the distal portion towards the direction of said pulled wire. Said rotation provides the desired lateral articulation.

FIG. 2B is a closer view of the lateral articulation mechanism 1000.

Figure 2C:
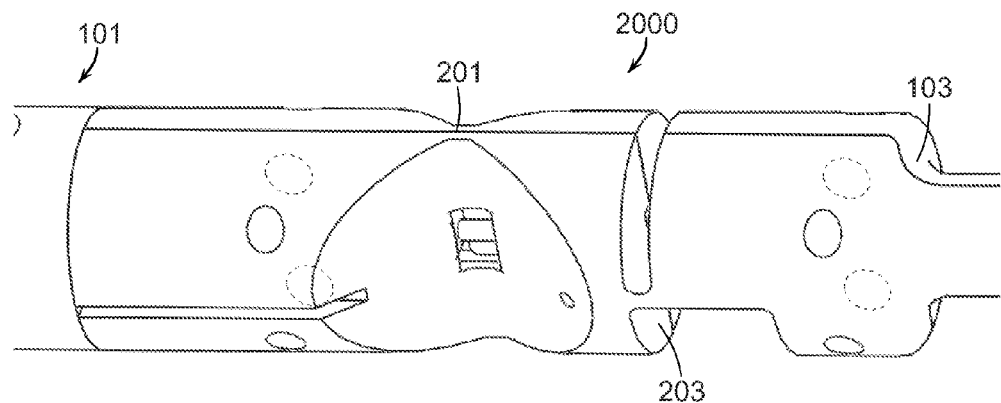
FIGS. 2C-2F illustrating an embodiment of the vertical articulation mechanism 2000.
Figure 2D:
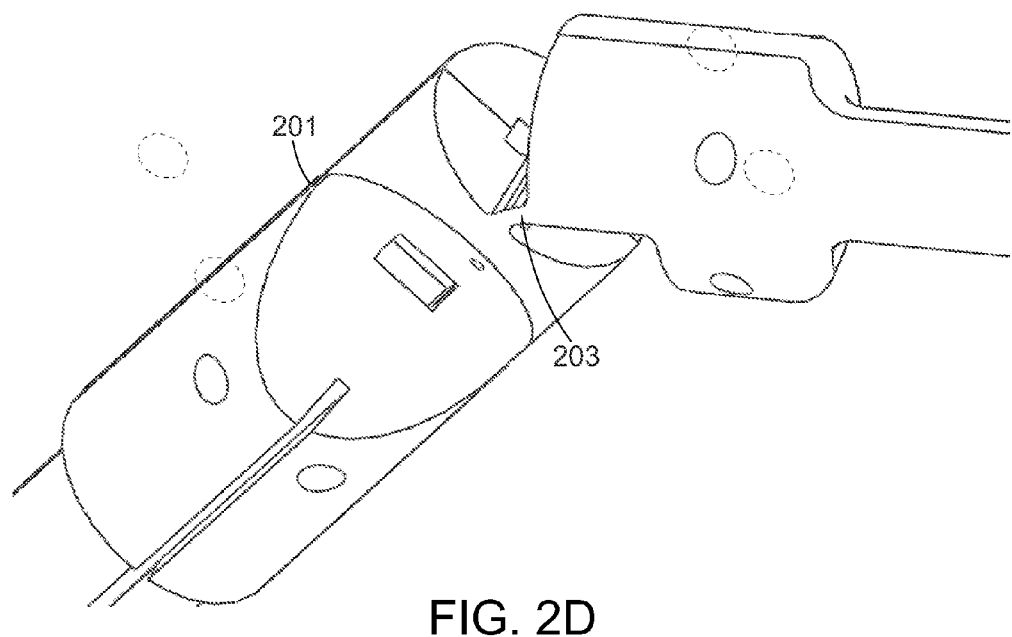

Reference is now being made to FIGS. 2C-2F illustrating an embodiment of the vertical articulation mechanism 2000. According to this embodiment, the vertical articulation mechanism 2000 comprises a connection 203, which functions as a hinge between tube 103 and the distal portion 101. Said vertical articulation is activated by pressing the distal portion 101 against the patient's tissue 204, therefore, generating a vertical rotation moment which vertically rotates the distal portion such that it is aligned to the tissue surface. FIG. 2C illustrates the ALDD without any vertical articulation and FIG. 2D illustrates the LADD with vertical articulation.

Figure 2E:
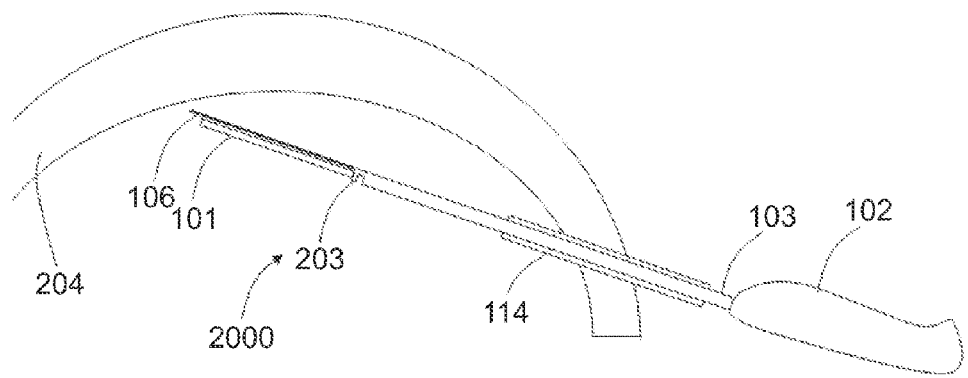
Figure 2F:
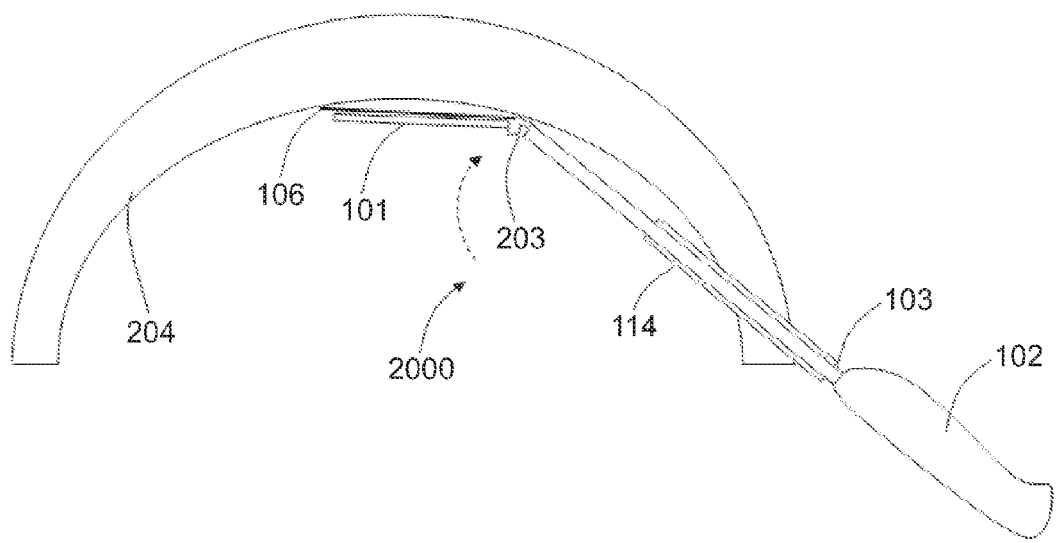

FIGS. 2E-2F illustrate the ALDD approaches the tissue 204 and presses against the same. As a result the ALDD is vertically articulated (see FIG. 2F).

It should be emphasized that the vertical articulation mechanism might be connected to the lateral articulation (1000) or directly to tube 103.

Reference is now made to FIGS. 2E-2F illustrating the activation of the vertical articulating mechanism 2000. Once the patch is deployed within the abdominal cavity, the deployment device is brought adjacently to the tissue 204 and pressed against it. Such pressing force vertically articulates the device so as the patch is optimally positioned against the hernia.

Reference is now made to FIGS. 3A-3D which illustrate the vertical articulating mechanism 2000 and the lateral articulation mechanism 1000.

Figure 3A:
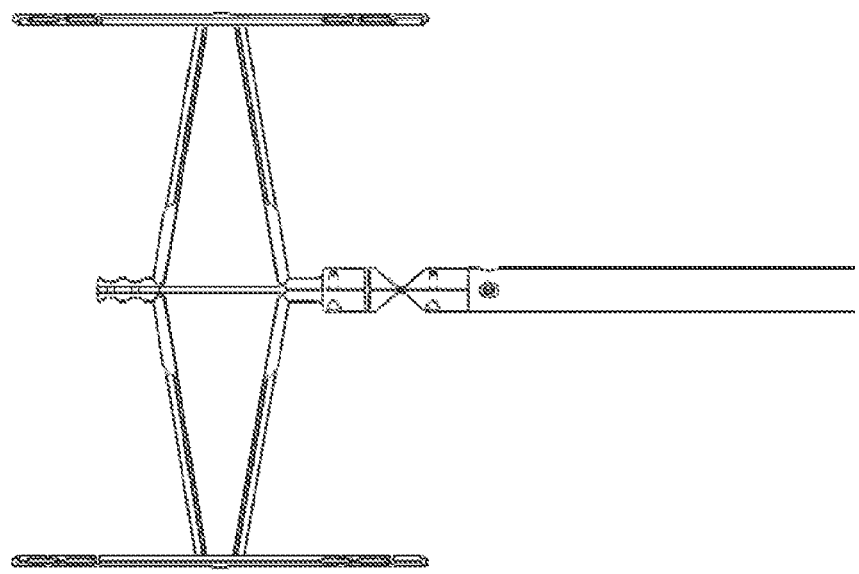
FIGS. 3A-3D illustrate the vertical articulating mechanism 2000 and the lateral articulation mechanism 1000.
Figure 3B:
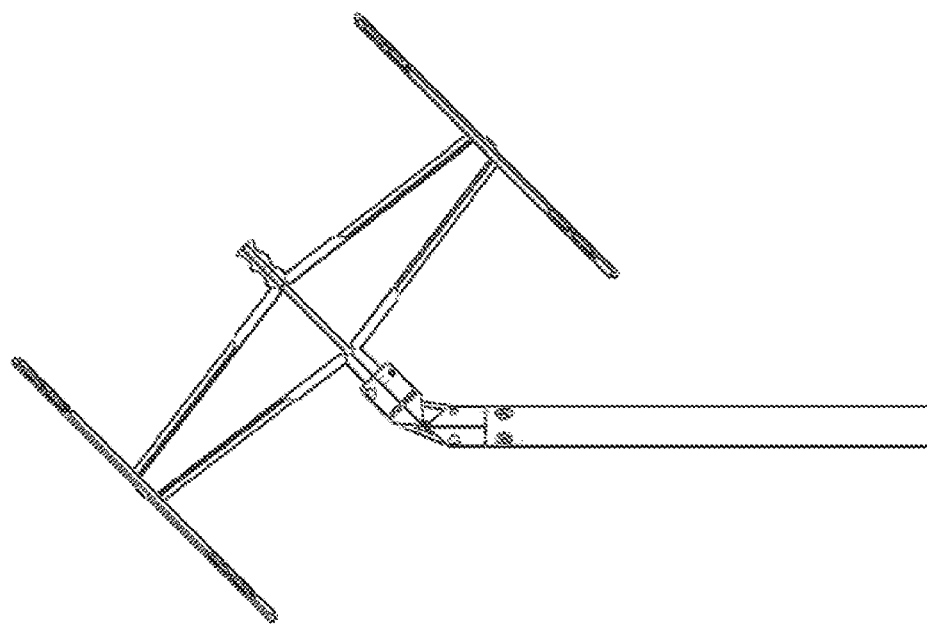

FIG. 3A illustrates the ALDD without any lateral articulation. FIG. 3B illustrates the ALDD laterally articulated.

Figure 3C:
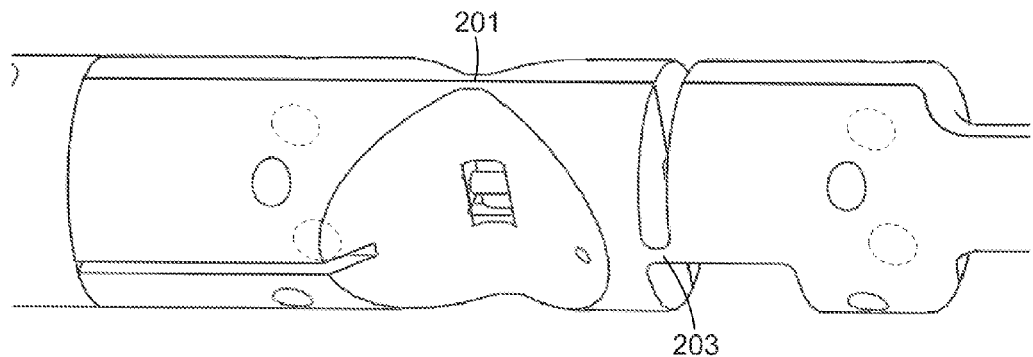

FIG. 3C illustrates the device without any vertical articulation. FIG. 3C illustrates the ALDD vertically articulated.

It should be emphasized that both the vertical and lateral articulation mechanisms can envelope at least a portion of the central shaft 105 when the ALDD is transformed from the closed configuration to the deployed configuration.

Figure 4:
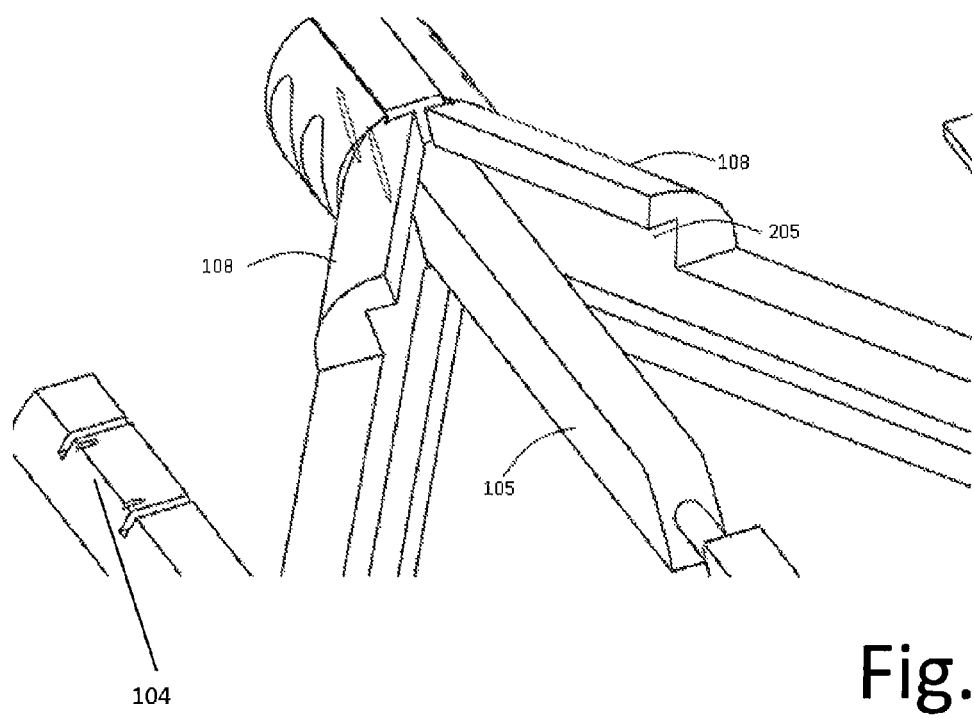
FIG. 4 illustrates an embodiment of the deployment arms 108.

Reference is now made to FIG. 4a which illustrates an embodiment of the deployment arms 108. While the patch 106 is rolled around the distal portion 101 and the distal portion 101 with the rolled mesh 106 is inserted into the patient's abdominal cavity, twisting and bending forces can be applied on the distal portion. Such forces may deform the distal portion and the DAs 108. Prevention of such deformation is illustrated in FIG. 4a. As can be seen in FIG. 4a, each of the DAs 108 comprises groove 205 such that, when the deployment device is in its closed configuration, the DAs 108 are enveloping the central shaft 105. Such enveloping provides a more rigid structure which can withstand said twisting and bending forces.

According to this embodiment, each DA 108 is composed of a groove 205 running along its length. Said groove 205 is fitted to the central shaft 106 such that when the distal portion is in its closed configuration the DAs 108 at least partially encapsulate the central shaft 105. As a result, as long as the distal portion is held in its closed configuration, the central shaft 105 serves as a back bone to the DAs 108, preventing major deformation when twisting and bending forces are applied.

Figure 5A:
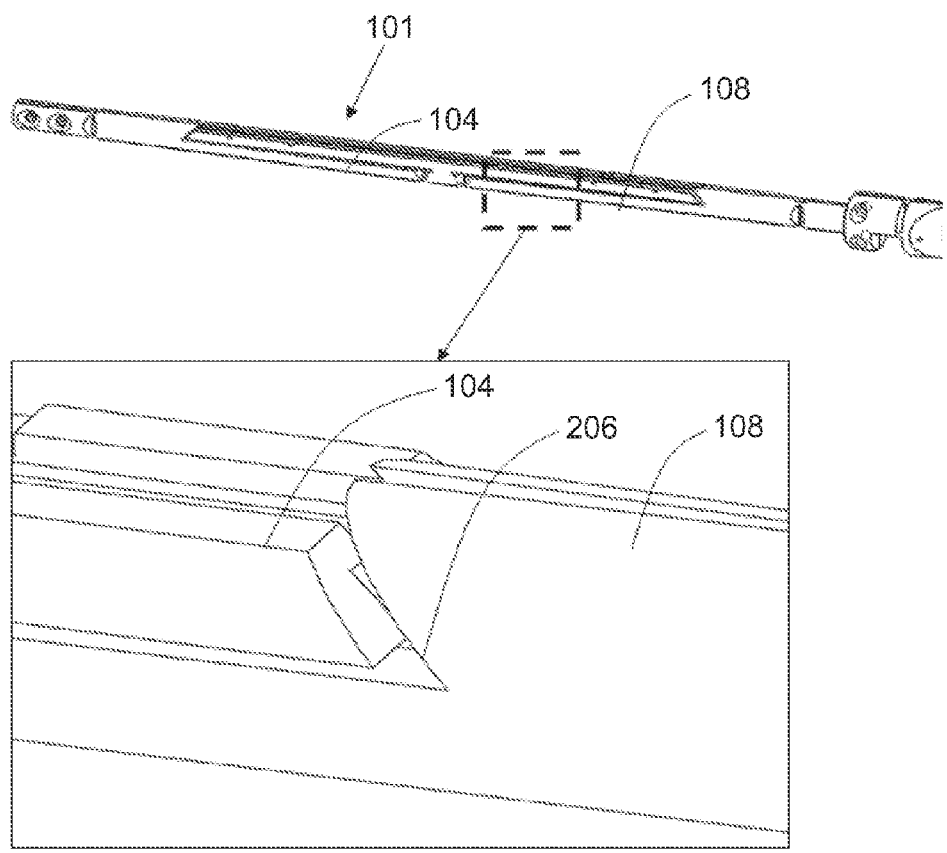
FIG. 5A illustrating another embodiment of the frame arms 104.

Reference is now made to FIG. 5A illustrating another embodiment of the frame arms 104. As was mentioned above twisting and bending forces are applied to the system during its normal operation. These forces may pull/push each FA away from the central shaft. As a result, the distal portion's cross section area is increased; and thus, prevents proper insertion of the patch 106 into the abdominal cavity.

Prevention of such improper insertion is enabled in FIG. 5A. As can be seen in FIG. 5A, the end portion of each FA 104 is inclined (tilted), creating a downward slope, the adjacent DA composed a tilted groove 206, such that the end of the FA 104 in fitted inside groove 206 while the distal portion 101 is in its closed configuration. As a result, groove 206 prevents improper movement of the FA 104.

Figure 5B:
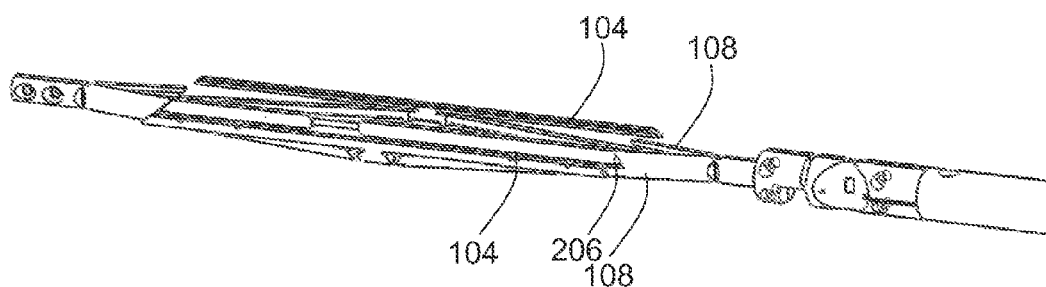
FIG. 5B illustrates the distal portion in its deployed configuration, in which the FA 104 are outside of groove 206.

FIG. 5B illustrates the distal portion in its deployed configuration, in which the FA 104 are outside of groove 206.

Figure 6A:
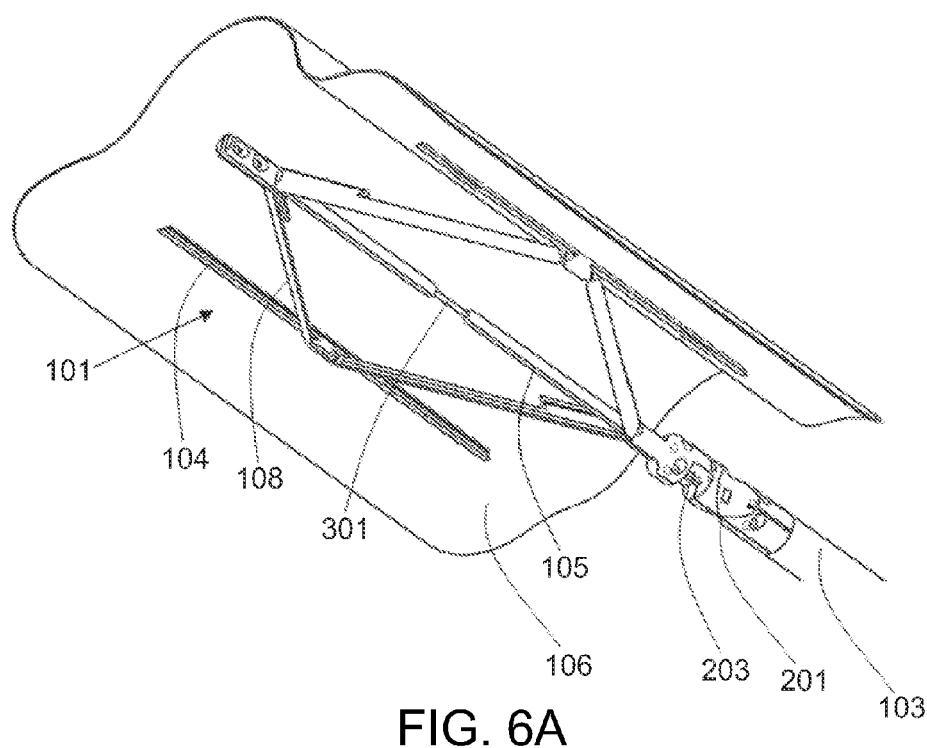
FIGS. 6A-6D describe an embodiments of the central shaft 105 that enables lateral and vertical articulations.
Figure 6B:
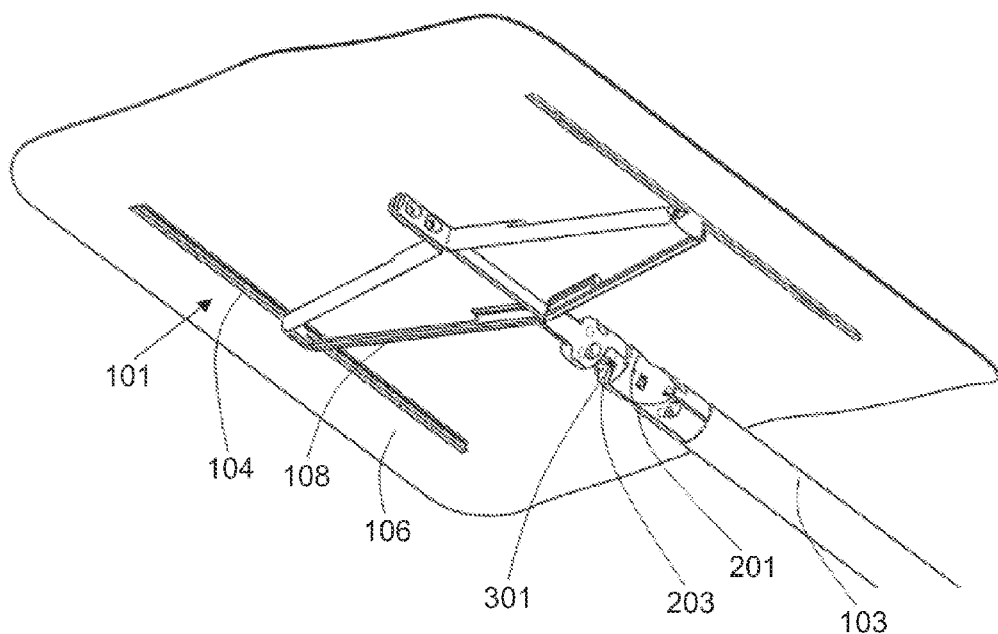
Figure 6C:
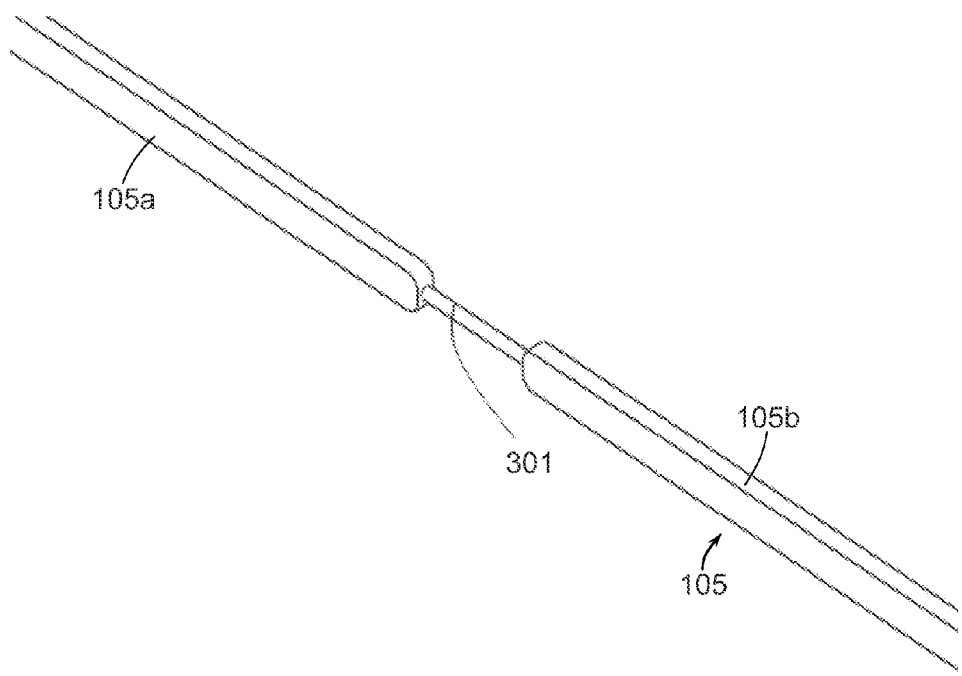
Figure 6D:
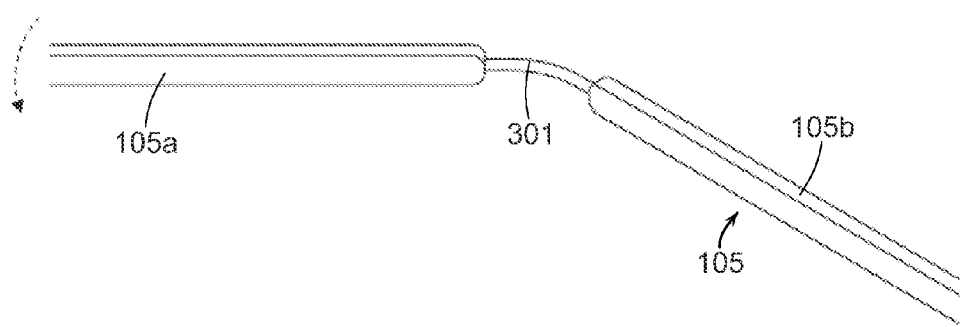

Reference is now made to FIGS. 6A-6C which describes an embodiments of the central shaft 105 enabling lateral and vertical articulations.

FIG. 6A illustrates the system in a semi-deployed configuration. In order to achieve said lateral and vertical articulations, the central shaft 105 comprises a flexibility region 301 that enables the lateral and vertical elastic bending.

Once the system is in its full deployed configuration (see FIG. 6B), the flexibility region 301 of the central shaft is pulled towards the proximal portion 102 and is positioned at the lateral and vertical articulation mechanisms (1000 and 2000 respectfully), therefore, once lateral and/or vertical articulation is activated, the distal portion of the central shaft 105 (i.e. distally to the flexibility region 301) can be rotated together with the distal portion 101 during said lateral and/or vertical articulation.

According to the embodiment describes at FIG. 6C, said flexibility region 301 is comprised of a flexible pin 301, connecting the distal and proximal portions (105a and 105b respectfully) of the central shaft 105.

Figure 3D:
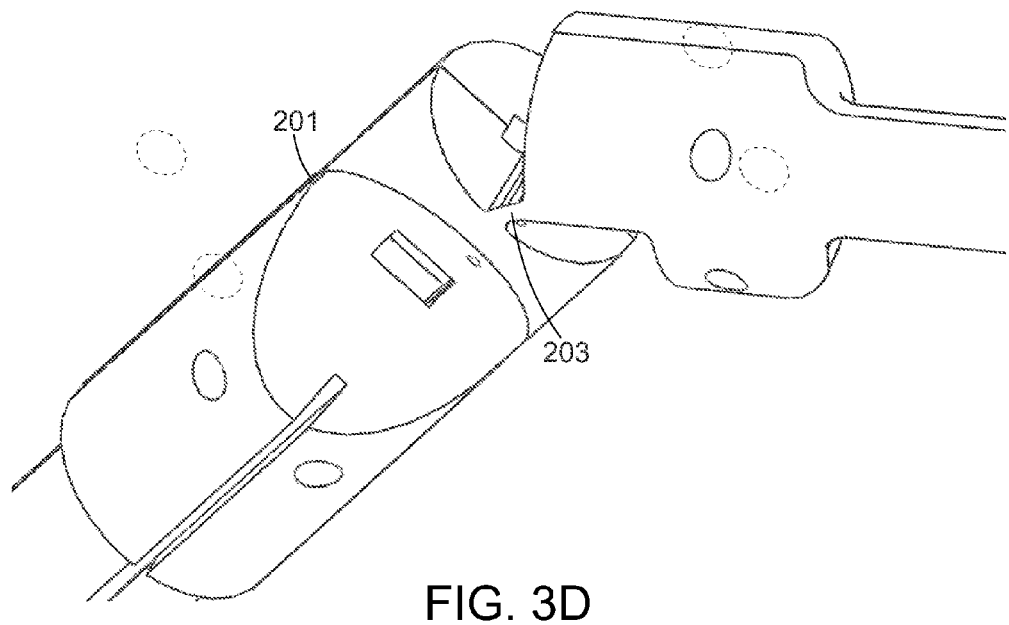

Said flexible pin 301 is made of elastic material (e.g. NiTi alloy-nitinol), such that it can be bended at up to 90 degrees to each direction without breaking or seriously deforming the same (FIG. 3D).

FIGS. 7A-7E illustrates another embodiment of the central shaft.

According to that embodiment the central shaft 105 comprises a flexible pin 304 connecting the distal and proximal portions of the central shaft 105 (105a and 105b).

Said flexible pin 304 is attached to the proximal portion 105a of the central shaft 105, and inserted into a hole at the distal portion 105b of the central shaft 105, such that a reciprocal motion (back and forth linear motion) between the two portions of the central shaft is enabled.

The flexible pin 304 is made of an elastic material (e.g. NiTi alloy-nitinol) and comprises a stopper 305 at its distal end, such that the two portion of the central shaft will remain connected once the distance between them reaches a maximal value.

Figure 7A:
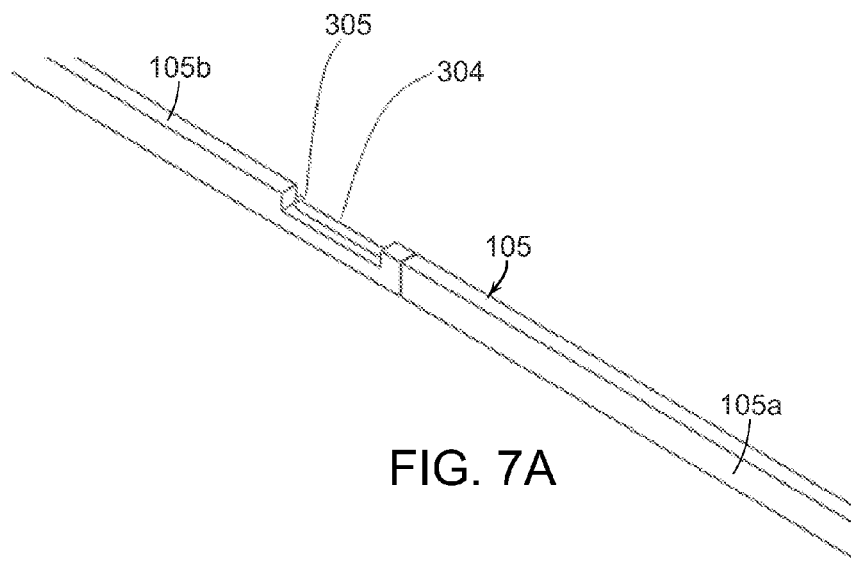
FIGS. 7A-7F illustrates another embodiment of the central shaft.
Figure 7B:
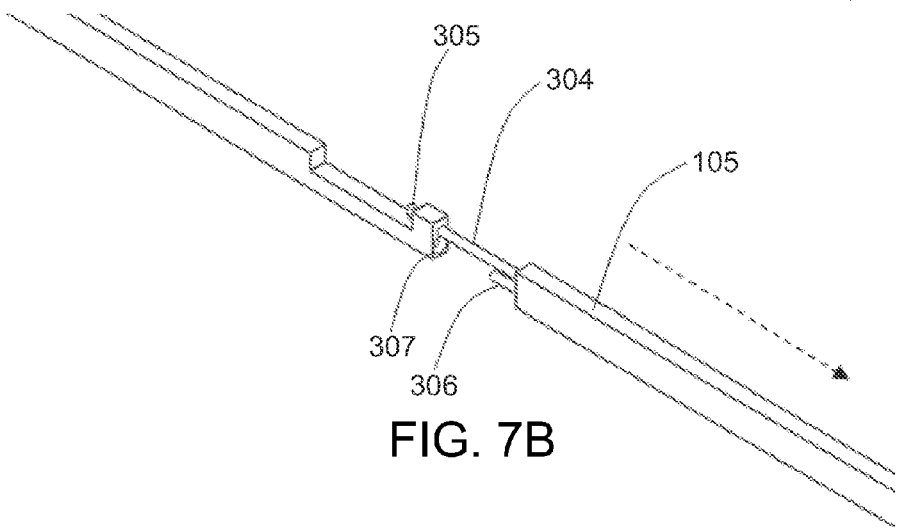
Figure 7C:
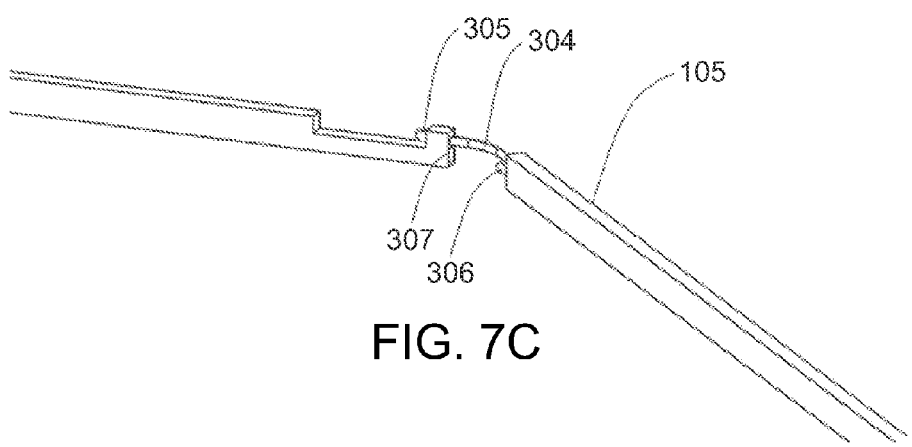

According to this embodiment the proximal portion 105a of the central shaft 105 additionally comprises a locking pin 306 which fits into a dedicated hole 307 in the distal portion 105b of the central shaft 105 (see FIG. 7B).

According to this embodiment, the central shaft can be characterized by two states: open state and closed state. The transformation between closed and open states is performed during the initial reciprocal movement of the central shaft 105. In the closed state (described at FIG. 7A), used once the distal portion 101 is in said closed configuration, the two portion of the central shaft are adjacent to one another; and the locking pin 306 is placed inside hole 307. As a result the central shaft can resist bending and twisting forces applied during patch rolling and insertion.

In the open state (described at FIG. 7B), the two portion of the central shaft are pulled apart from each other, such that the locking pin 306 is located outside hole 307 and the flexible pin 304 is the only member connecting between the portions of the central shaft (105a and 105b). As a result the desire flexibility of the central shaft is achieved and lateral/vertical articulation is enabled (see FIG. 7C).

Figure 7D:
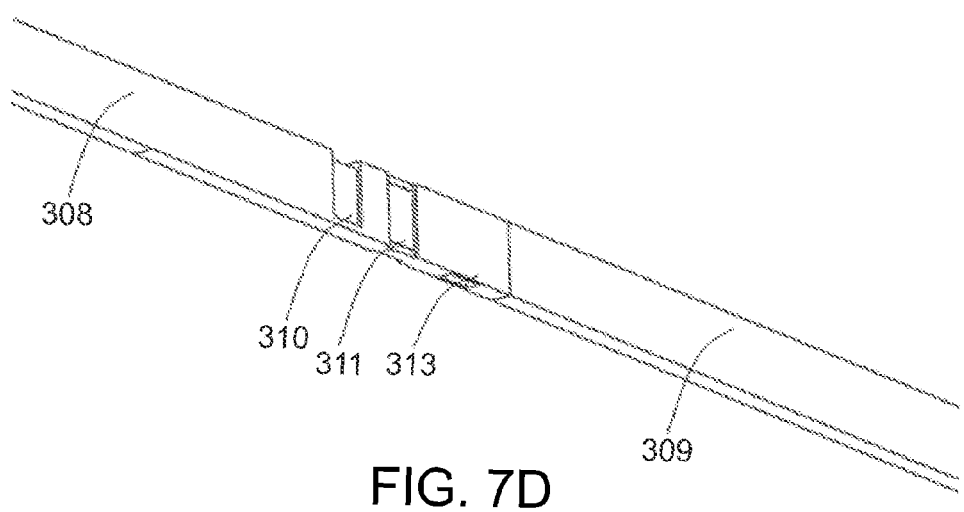
Figure 7E:
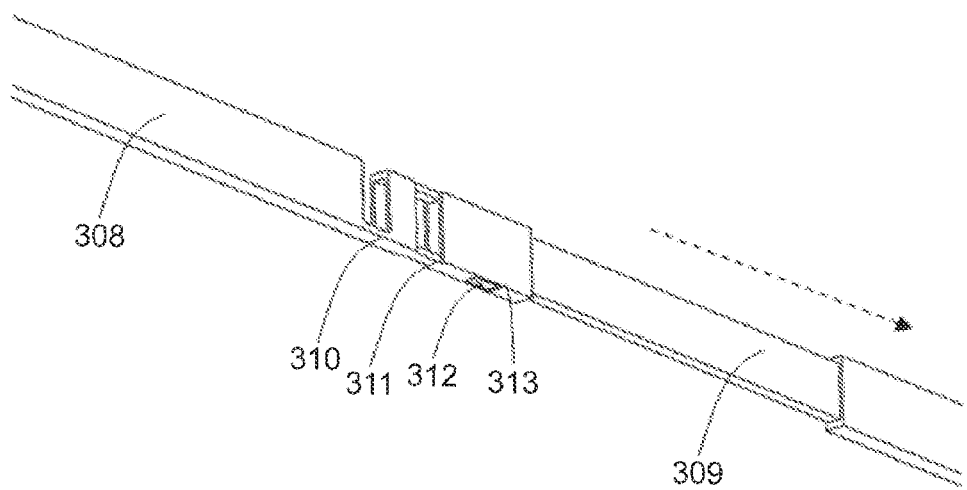
Figure 7F:
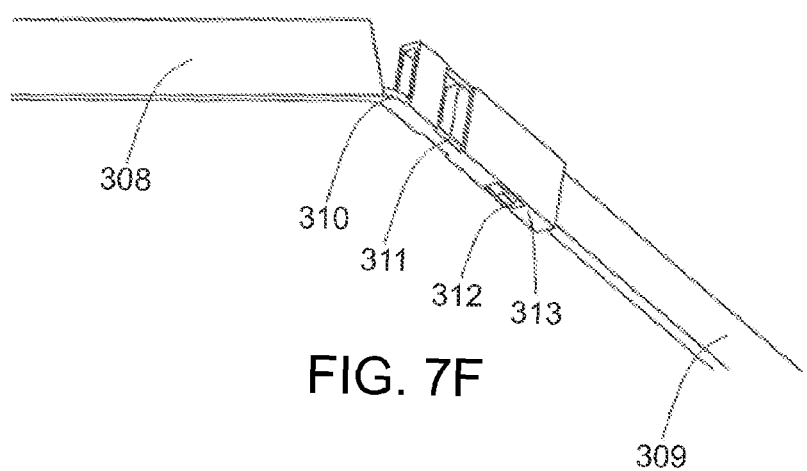

FIGS. 7D-7F illustrates yet another embodiment of the central shaft 105. This embodiment is also characterized by open and closed states. According to this embodiment the central shaft is composed of a distal portion 308 and a proximal portion 309. The distal portion 308 comprises an elongated sleeve adapted to envelope the proximal portion 309.

Additionally, the distal portion 308 comprises vertical articulation region 310, characterized by increased flexibility in the vertical direction and lateral articulation region 311, characterized by increased flexibility in the lateral direction.

FIG. 7D illustrates the central shaft in its closed state, wherein the proximal portion 309 is completely inserted into the distal potion. As a result, the central shaft 105 is characterized with high resistance to bending and twisting forces which implemented while the distal portion is in its closed form.

The proximal portion 309 comprises a stopper 312, adapted to be inserted into a stopper slot 313 at the distal portion 308. During the initial reciprocal movement of the central shaft 105, the proximal portion 309 slides out of the distal portion 308 until said stopper 312 is inserted into the stopper slot 313. Once the stopper is inserted into the slot disengagement between the two parts of the central shaft 105 is prevented.

When the central shaft 105 is in its open state, it is characterized by a greater vertical and lateral flexibility. Such flexibility is obtained by superimposing and aligning the central shaft vertical articulation region 310 and lateral articulation region 311 with the vertical articulation hinge connection 203 and the lateral articulation hinge connection 201.

As described above, FIG. 7D illustrates the central shaft in its fully closed state, FIG. 7E, FIG. 7E illustrates the central shaft in its fully opened state (in which it is highly flexible), and FIG. 7F illustrates the central shaft in its fully opened state and vertically bended.

Figure 8A:
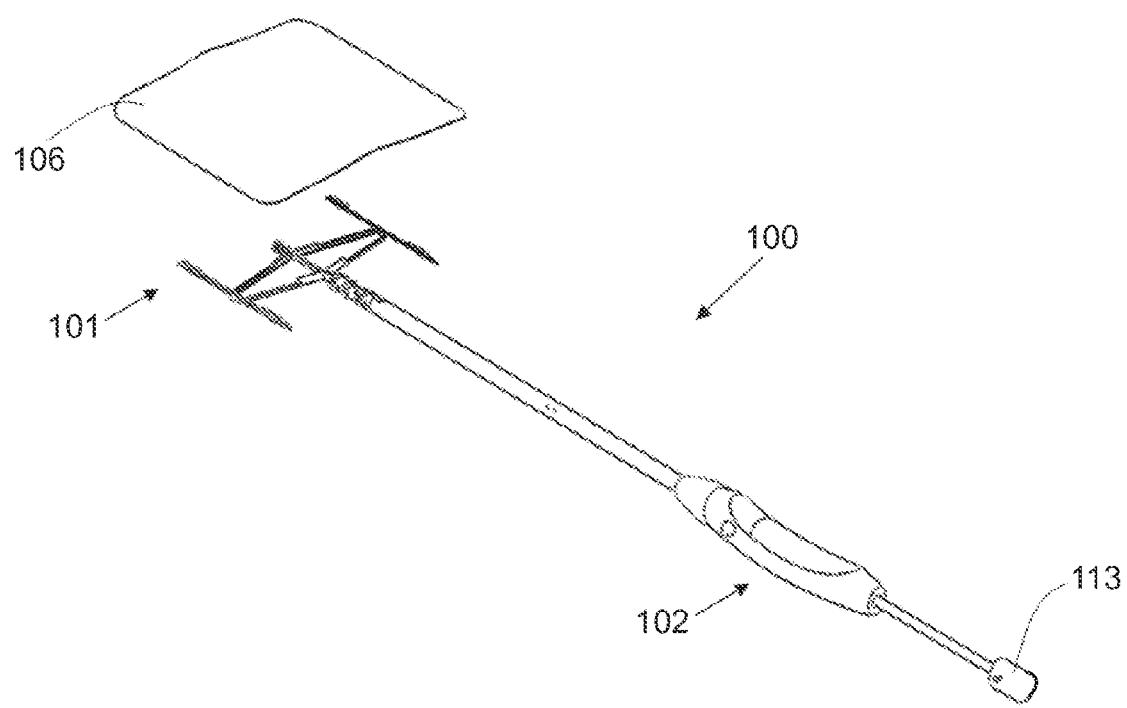
FIGS. 8A-8M illustrate a method utilizing the ALDD 100.
Figure 8B:
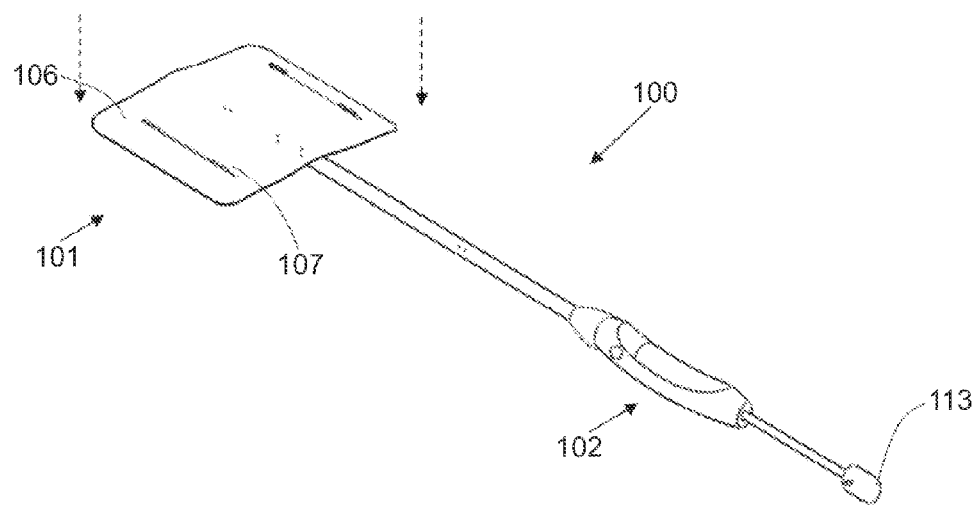
Figure 8C:
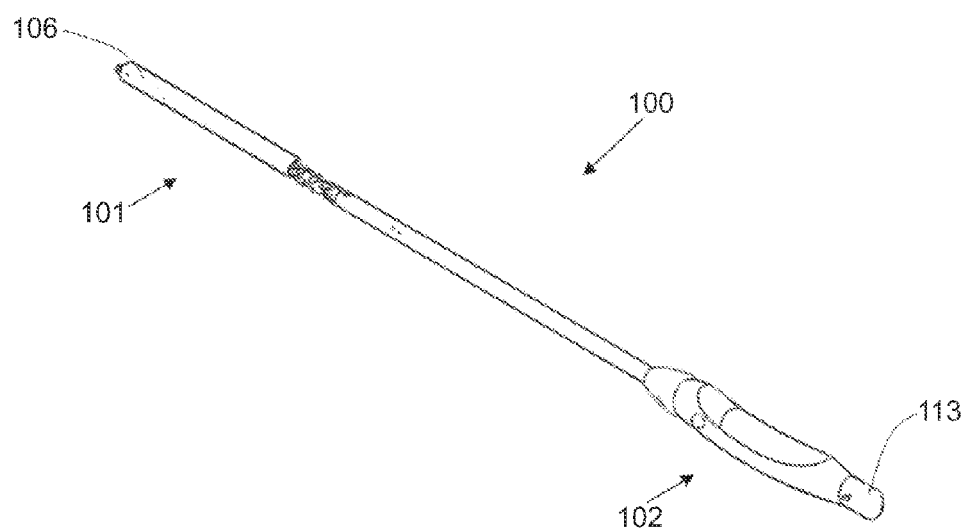
Figure 8D:
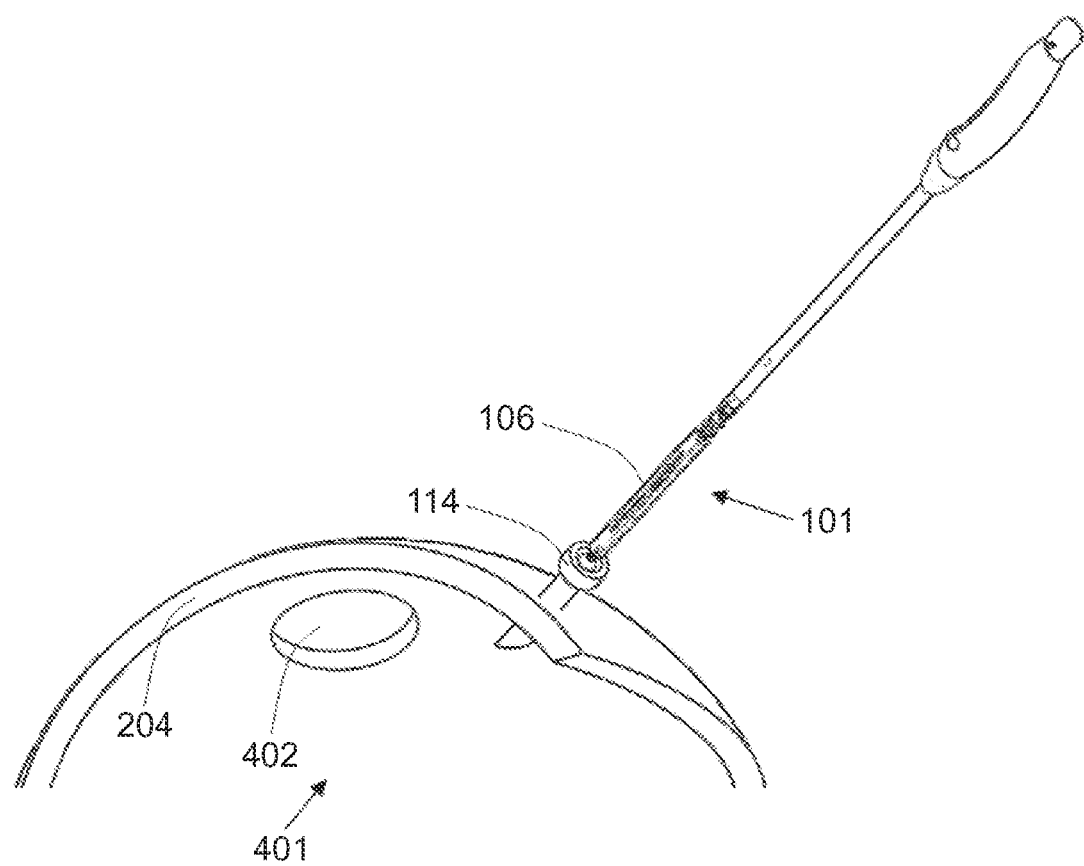
Figure 8E:
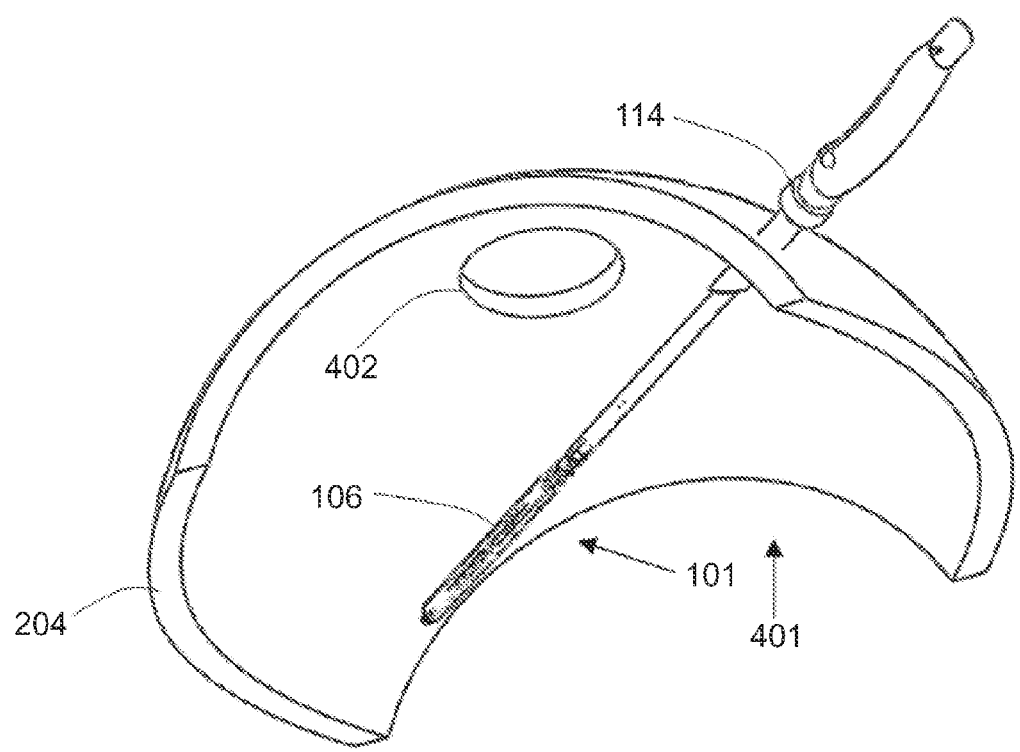
Figure 8F:
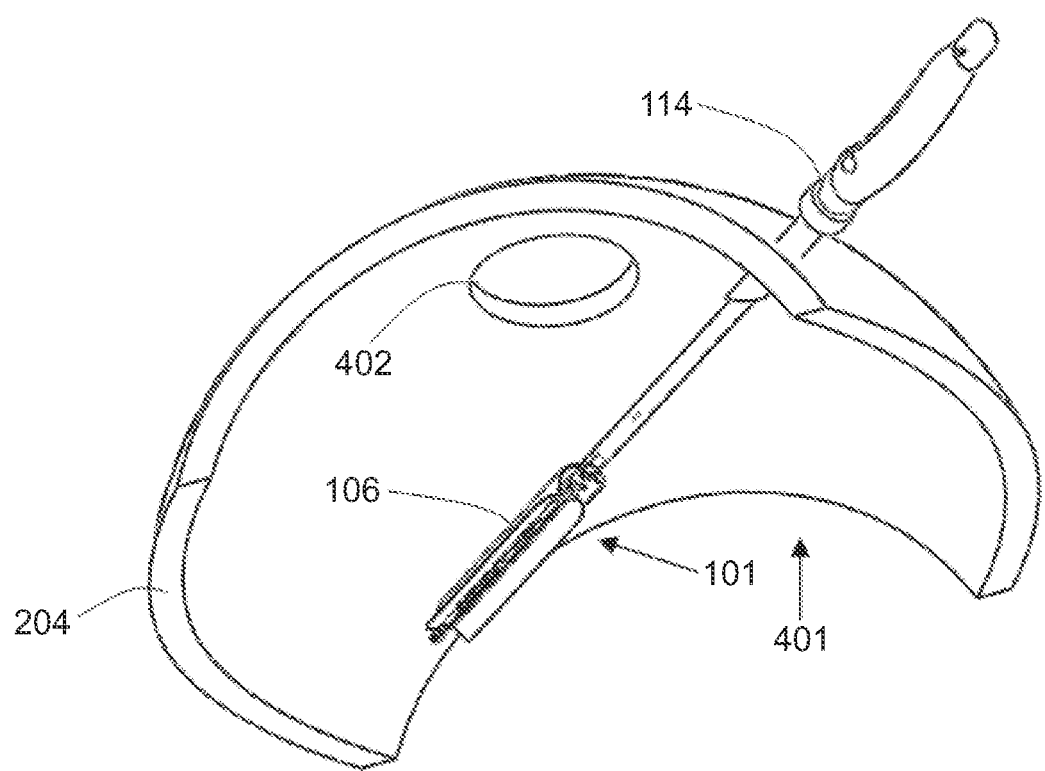
Figure 8G:
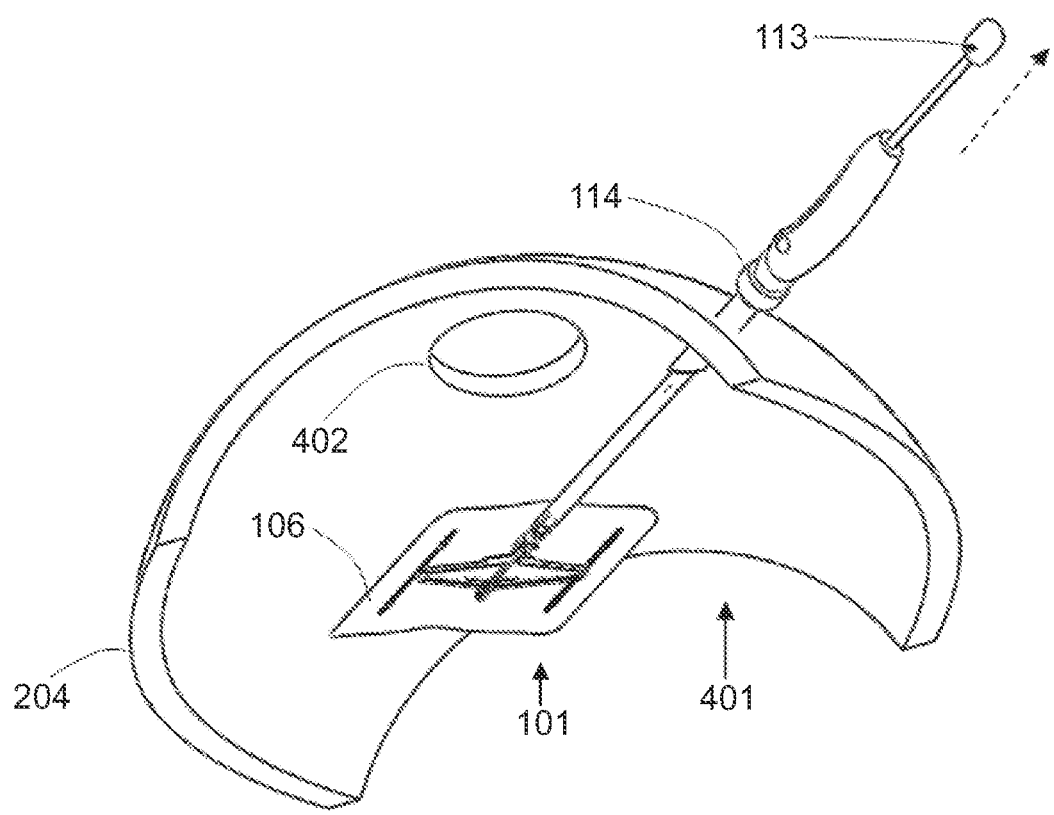
Figure 8H:
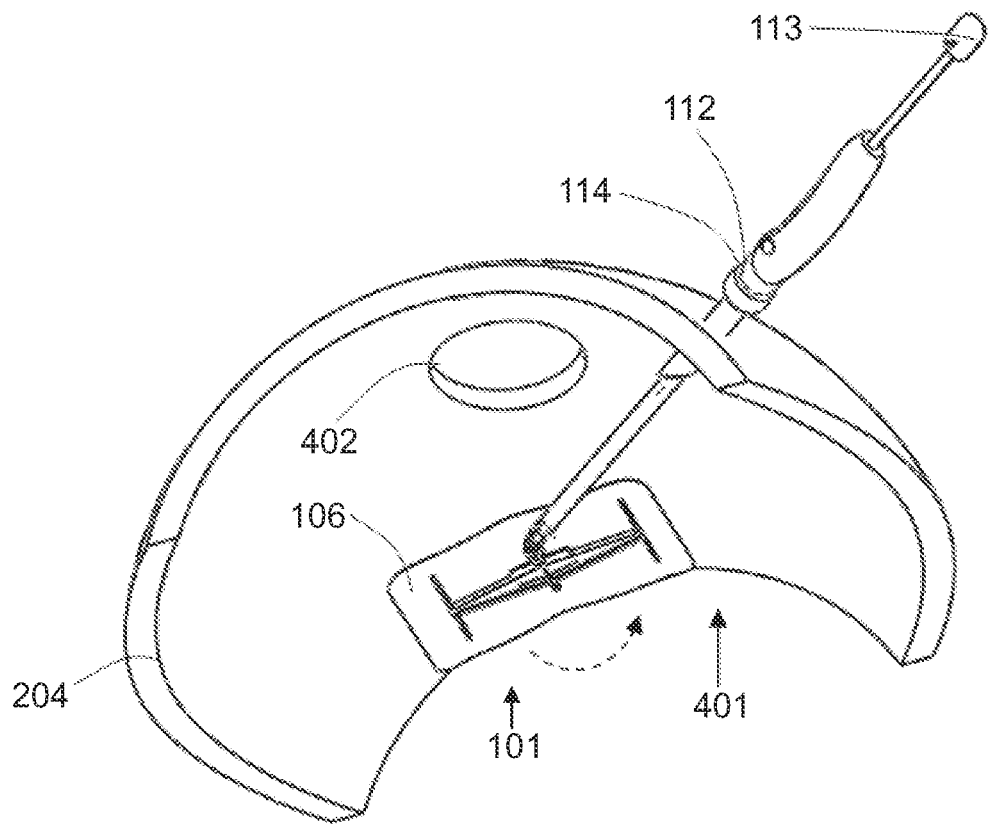
Figure 8I:
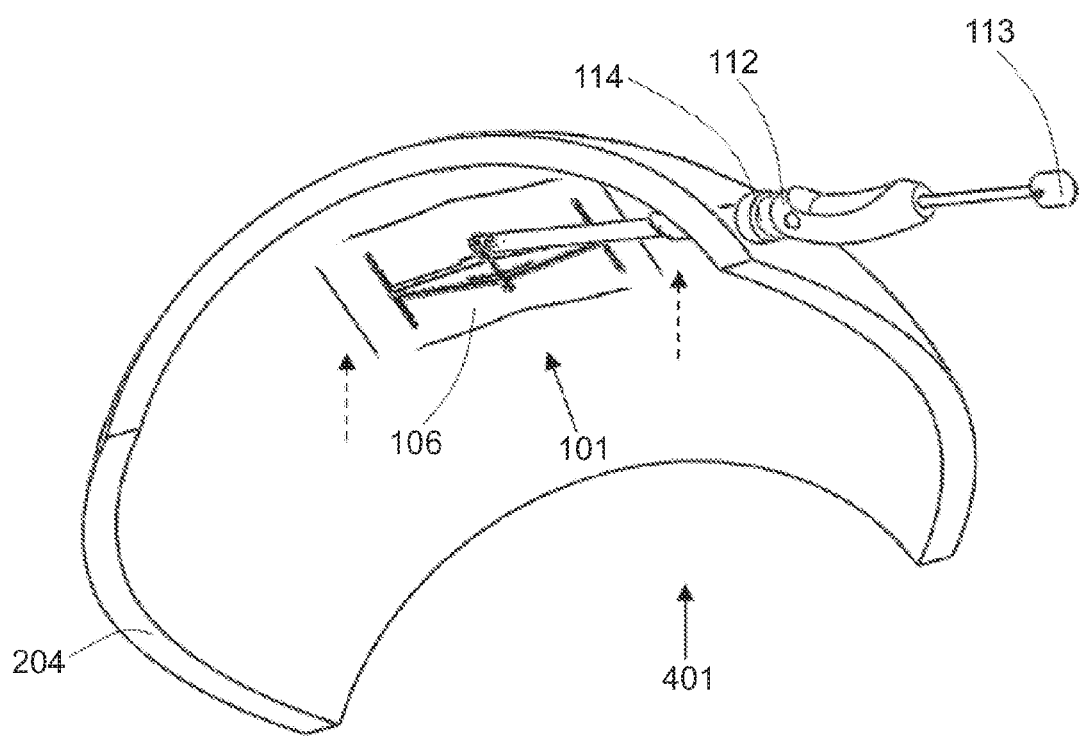
Figure 8J:
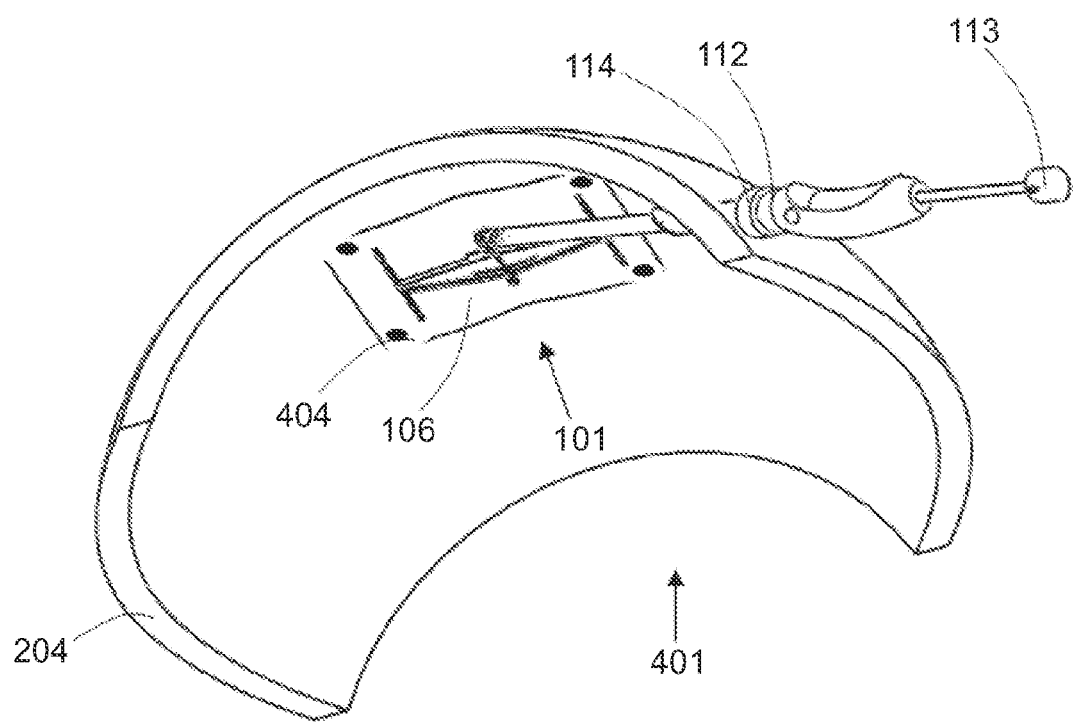
Figure 8K:
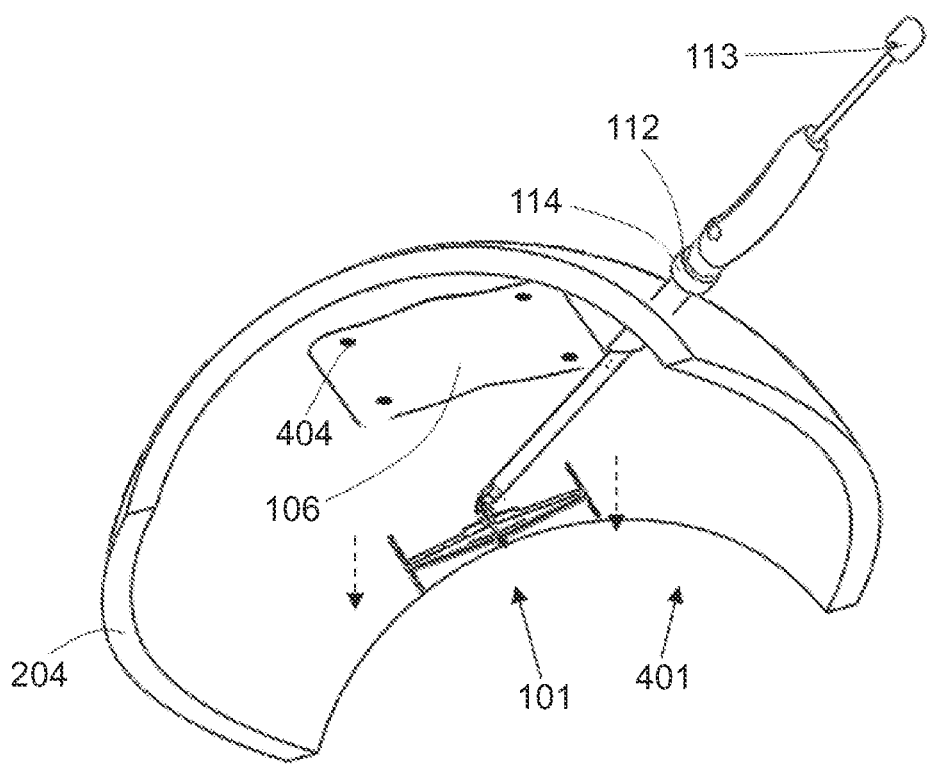
Figure 8L:
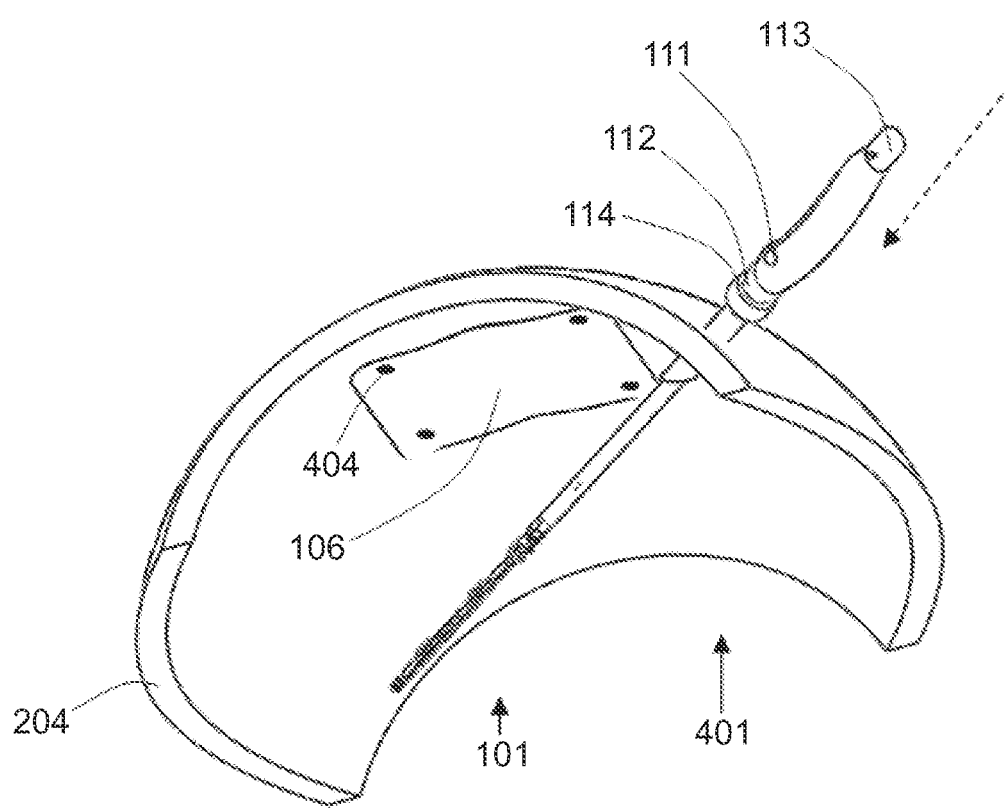
Figure 8M:
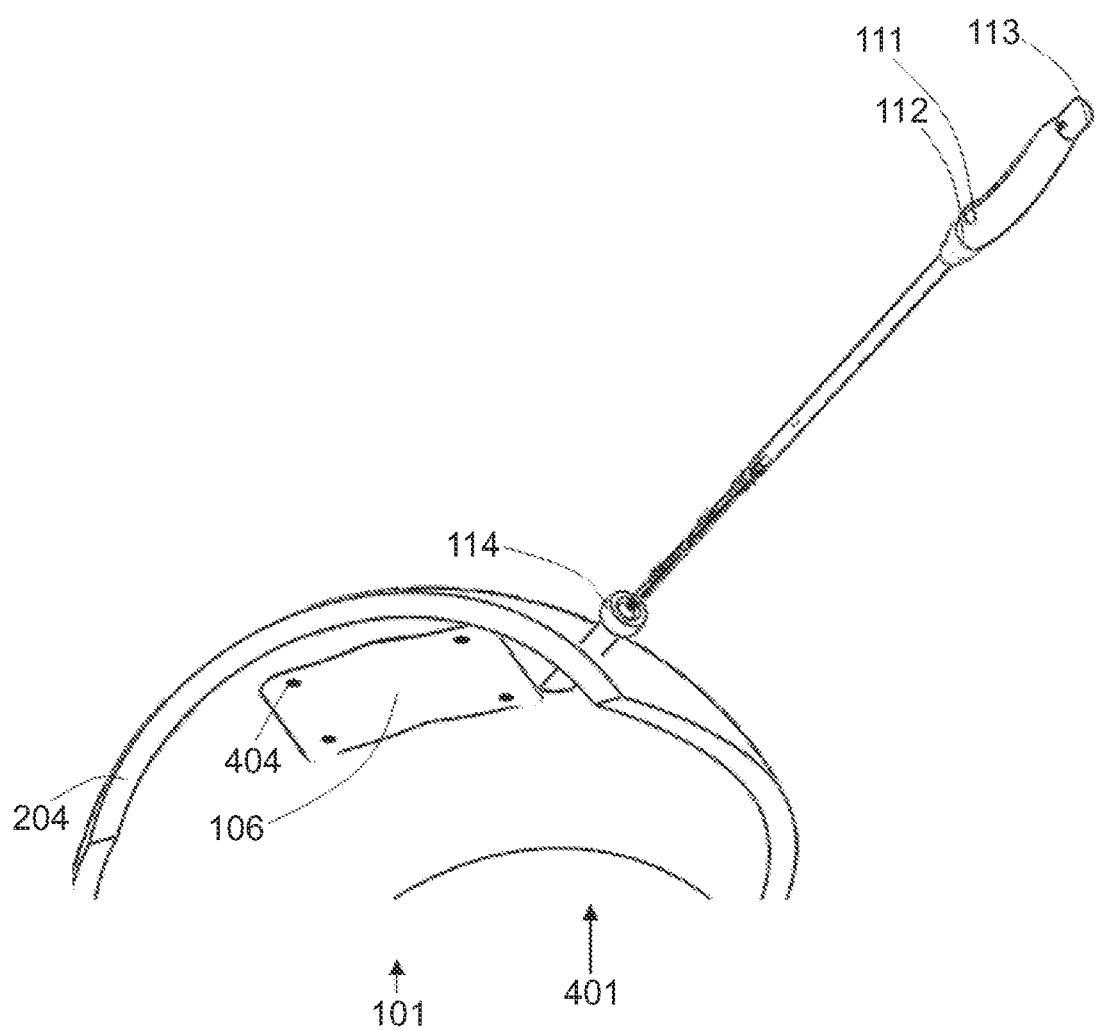

Reference is now made to FIGS. 8A-8M which describes a method utilizing the ALDD 100 (as described above) during a laparoscopic hernia repair surgery. The method comprises steps selected inter alia from:

1. Obtaining a prosthetic patch 106, and an ALDD 100 in its open state (FIG. 8A).
2. Attaching patch 106 to the distal portion 101 of the ALDD 100 (FIG. 8B).
3. transforming the ALDD 100 from its open configuration (deployed configuration) to its closed configuration using the deployment lever 113 (FIG. 8C).
4. Rolling the patch 106 onto the distal portion 101 (FIG. 8C).
5. Inserting the distal portion 101 together with the rolled patch 106 into the patient's abdominal cavity 401 trough the trocar 114 (FIGS. 8D,8E).
6. Unrolling the patch 106 by slightly shaking the distal portion 101 or via a grasper (FIG. 8F)
7. Spreading (deploying) patch 106 by transforming the distal portion 101 from its closed configuration to its open configuration using the deployment lever 113 (FIG. 8G).
8. Laterally rotating the distal portion 101 and hence patch 106, using the articulation lever 112, until it reaches the proper orientation of the patch with regards to the hernia defect 402 (FIG. 8H)
9. Elevating the distal portion to proximate the hernia defect, and verifying correct location of the patch 106 with regards to the hernia defect.
10. Correcting the location and/or the orientation of the patch, if necessary.
11. Pressing the distal portion 101 and the patch 106 against the patient's tissue 204 near the hernia defect 402 until the distal portion 101 is proximally aligned with the patient's tissue 204 around the hernia defect 402 (FIG. 8I).
12. Attaching the patch 106 to the patient's tissue 204 using attachment mean 404—e.g. hernia tacks, sutures (FIG. 8J)
13. Disengaging the distal portion 101 from the patch 106 and removing the distal portion 101 away from the patch 106 (FIG. 8K).
14. Rotating back the distal portion 101 into its initial straight lateral angle using the articulation lever 112.
15. Transforming the distal portion 101 from its deployed configuration to its closed configuration (FIG. 8L).
16. Extracting the distal portion out of the patient's abdominal cavity 401 (FIG. 8M).

Said patch location verification describe in step 9 can be performed by a number of different mechanisms.

If the patch 106 is transparent enough to observe the hernia defect 402 trough it, the patch 106 can be move to its desired location while it is close to or slightly pressed against the tissue, prior to attachment between the patch 106 and the patient's tissue 204. The surgeon, using the laparoscopic camera, can verify that there are sufficient margins between the hernia defect 402 edges and the patch 106 edges.

If the patch 106 is not transparent enough to enable observation of the hernia defect 402 through it, the patch 106 location can be verified by bridging it approximately to the optimal location, and then lowering it a few centimeters down to a point in which the hernia defect 402 can be viewed together with the patch 106. then the location can be adjusted. Once the patch is in its correct location it can be raised and presses to the tissue.

Yet another method to verify the location of patch 106 is to first mark the center of the patch 106 and the center of the hernia at the patient's skin surface, prior to patch insertion. Once the mesh is inserted and deployed, a long needle is inserted through the marked center of the hernia defect into the abdominal cavity, then the patch 106 in brought in contact with the needle edge, such that it touches the pre-marked point on the patch's surface. The patch can be elevated into its location while keeping the needle in the center point. Alternatively, the surgeon can use his/her finger in order to create a bulge in the center of the hernia, to which he/she can bring the center of the patch, while elevating it into contact with the patent's tissue 204.

Reference is now made to FIGS. 9A-9D which illustrate another embodiment of the lateral articulating mechanism (3000). According to this embodiment a shaft 110 is coupled to tube 103 and to the proximal DAs 108*c* and 108*d*.

The lateral articulation is performed using the same hinges which connect the distal DAs 108*c* and 108*d* to the central shaft 105 and hinges which connects the proximal DAs 108*a* and 108*b* to shaft 110.

The two distal DAs 108 are connected to the central shaft 105 using a single pin 501 which serves as a hinge (see FIG. 9A2).

Each one of the proximal DAs has a semi open ring 502, such that eventually, when the ALDD is in the deployed configuration, pin 501 is threaded through the open portion of said two rings 502.

In addition, the proximal end of tube 103 comprises a tube 503 which is vertically positioned with respect to said tube 103. Tube 503 comprises an open portion.

Figure 9B:
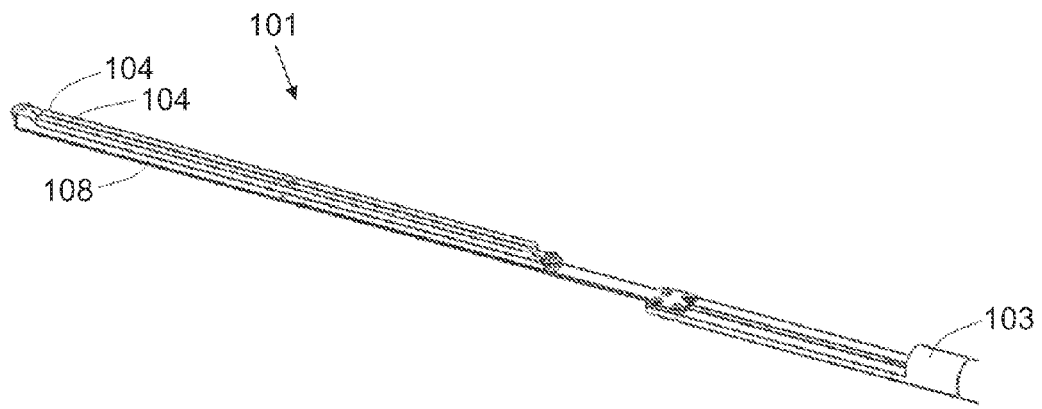
Figure 9C:
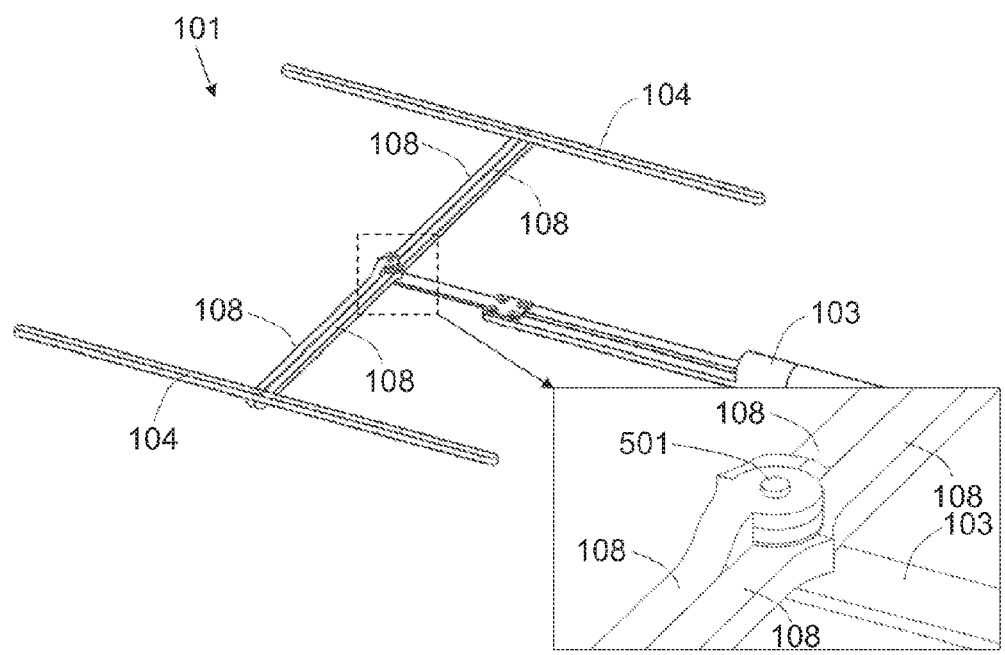
Figure 9D:
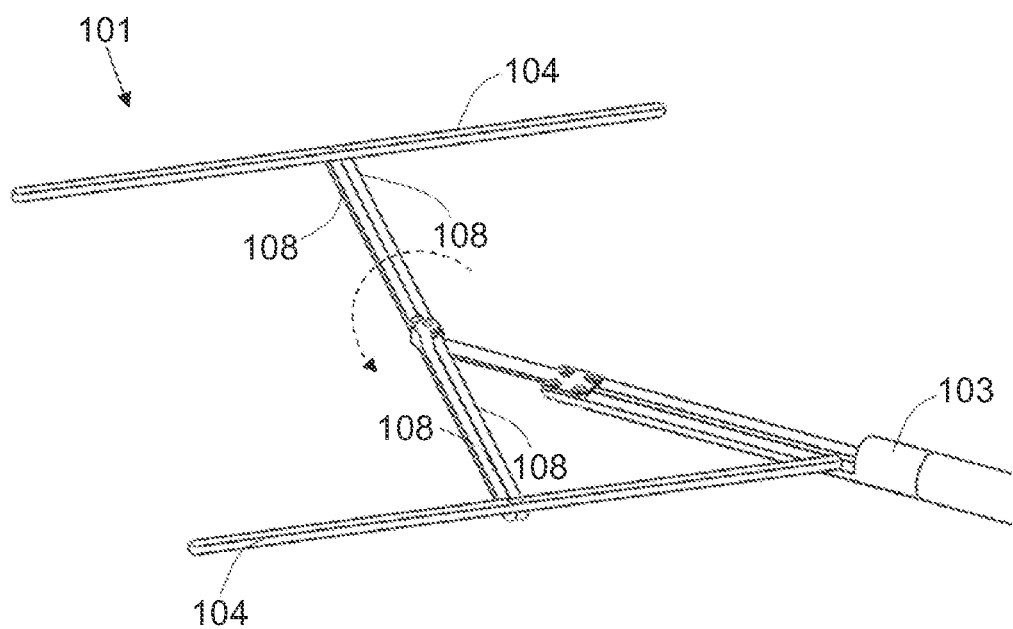

Each of the rings 502 at least partially encapsulate tube 503; such that said tube 503 serves as a hinge between the two proximal DAs 108 and tube 103 (see FIG. 9A3). Once the distal portion 101 is transferred to its closed configuration, pin 501 is inserted into the center of tube 503 through the opening in said tube 503 and said opening is said two rings 502 (FIG. 9C). As a result the center of the distal hinge and the proximal hinge are combined. As a result the two hinges are practically serves as a single hinge (see FIG. 9C), which can be used for the lateral articulation of the entire distal portion 101 (FIG. 9D).

Figure 9E:
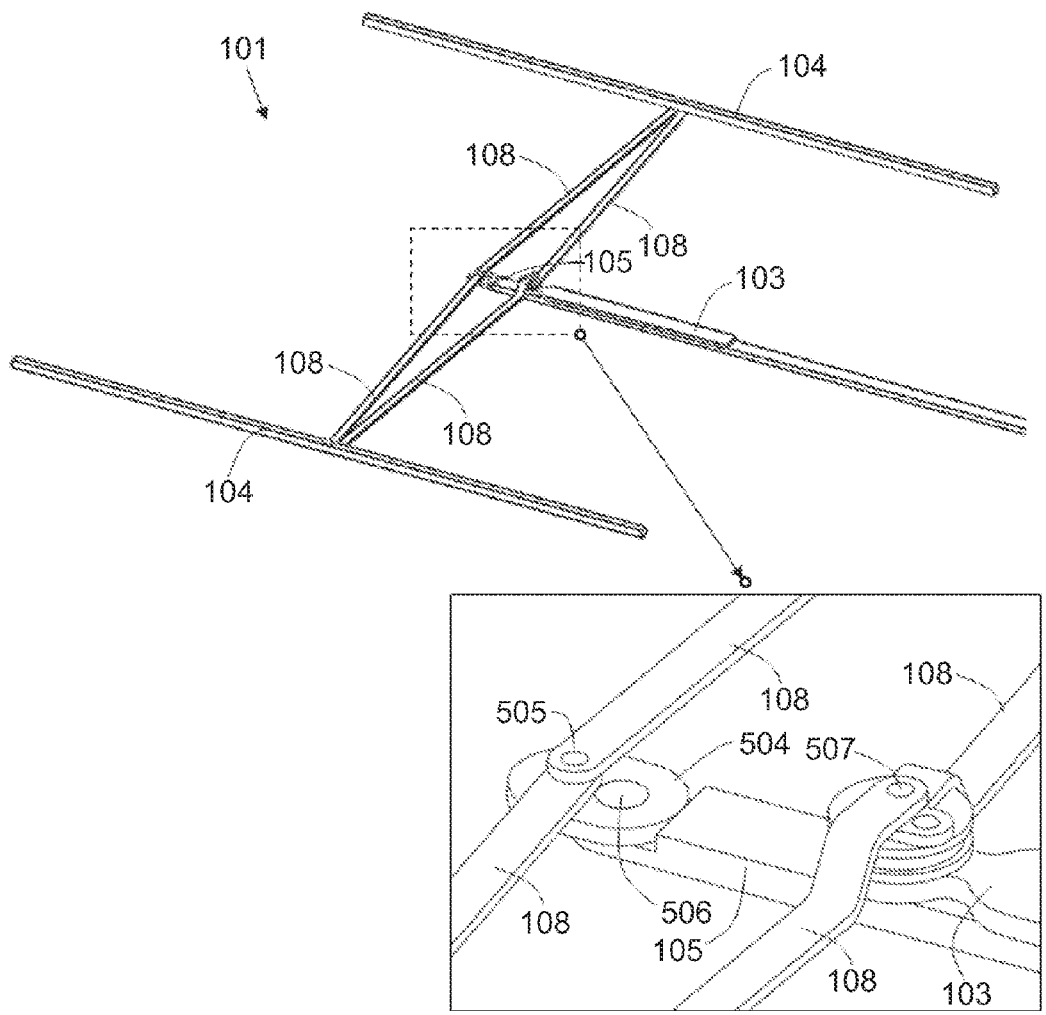
FIGS. 9E-9F illustrate another embodiment of the lateral articulating mechanism (4000).
Figure 9F:
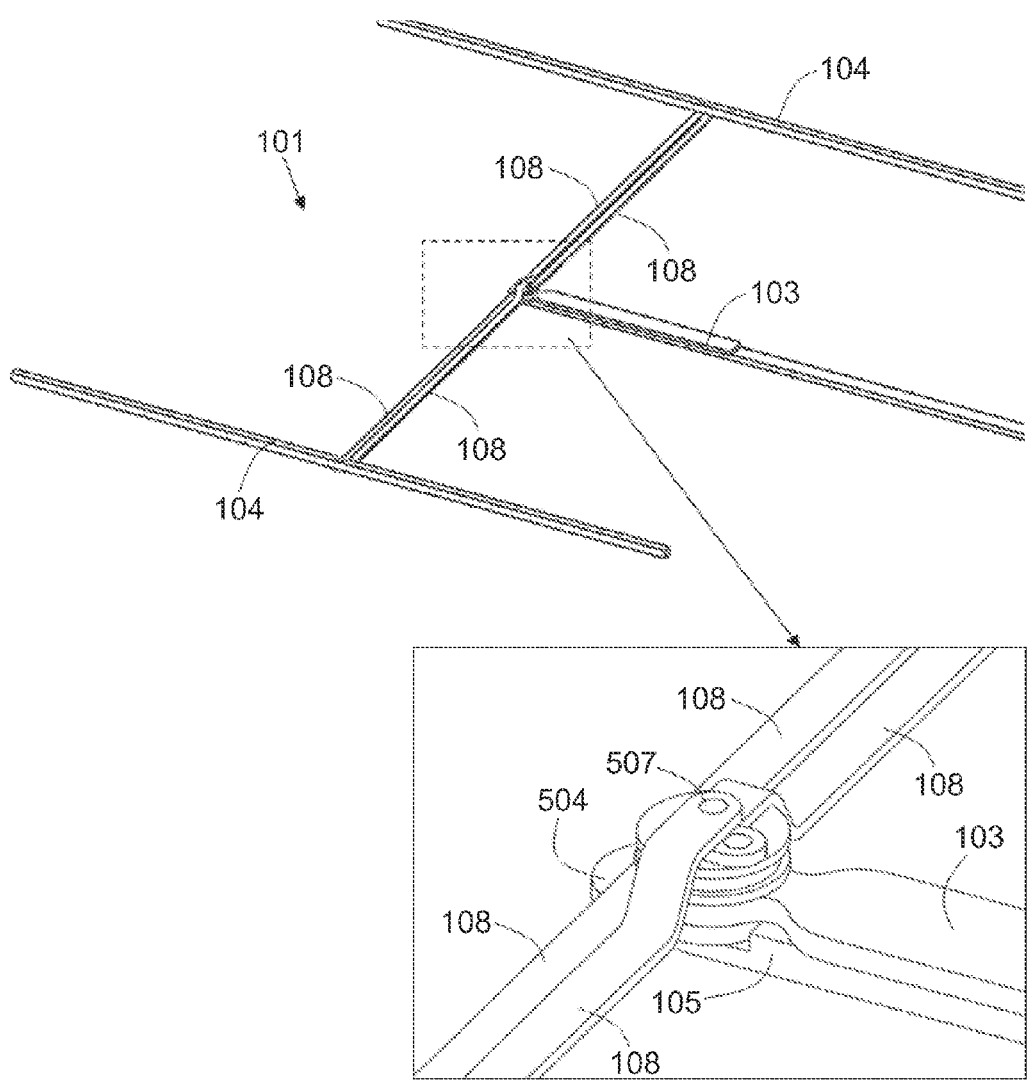

Reference is now made to FIGS. 9E-9F which illustrate another embodiment of the lateral articulating mechanism (4000).

According to this embodiment, the distal DAs 108 are connected to a plate 504 by a single pin 505 which serves as a hinge. The plate 504 is connected to the central shaft 105 by another pin hinge 506 located proximally to the pin 505 (FIG. 9E).

The proximal DAs 108 are placed on top of each other and are connected to the distal end of tube 103 by a pin 507 which serves as a hinge.

Once the distal portion 101 is transferred into its closed configuration, the centers of pins 506 and 507 are aligned, therefore they now serve as a single hinge enabling the lateral articulation of the distal portion 101 (FIG. 9F).

Figure 10A:
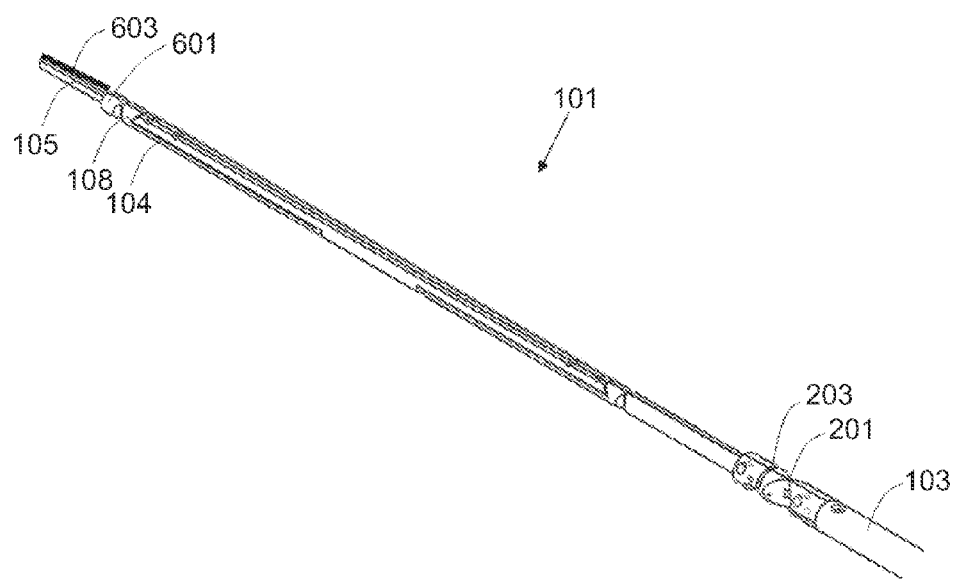
FIGS. 10A-10B illustrate another embodiment of the distal portion 101.
Figure 10B:
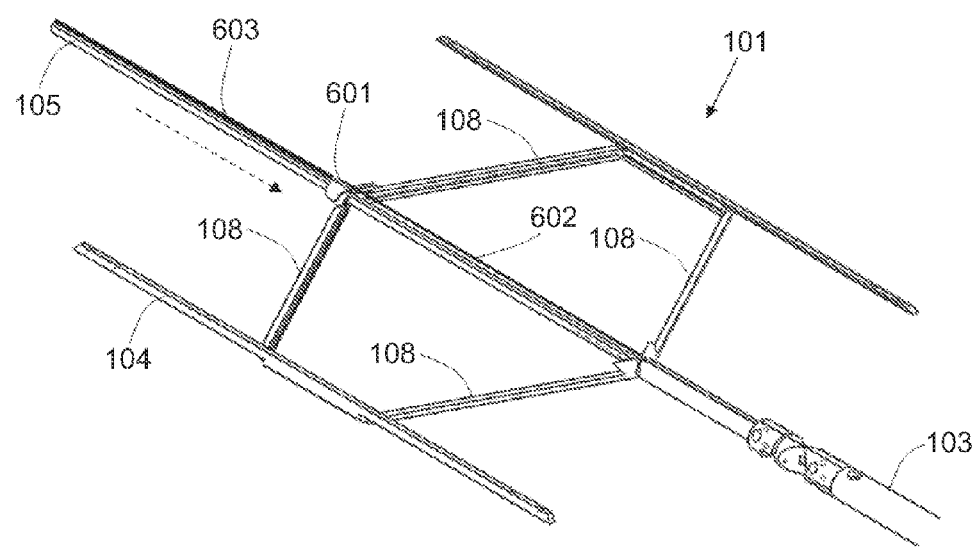
Figure 11:
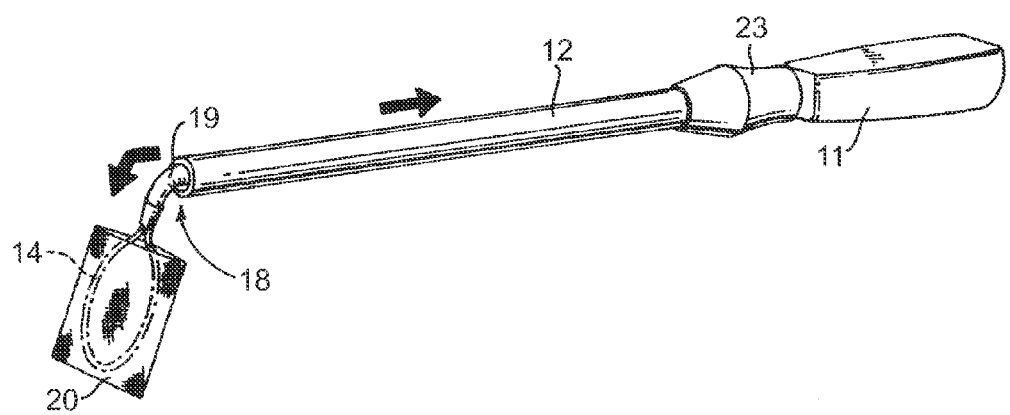
FIG. 11 illustrates prior art teaching.

Reference is now made to FIGS. 10A-10B which illustrate another embodiment of the distal portion 101. This embodiment enables articulation prior to the deployment of patch 106. Such an embodiment enables an improved maneuverability if a large patch (i.e. larger then 20 cm) is utilized.

According to this embodiment, the central shaft 105 is coupled to tube 103 and the distal DAs 108c and 108d are connected., to a deployment cart 601 (instead the central shaft 105) which is adapted to slide along the central shaft 105. Cart 601 is connected at its proximal end to an elongated deployment wire 602 threaded trough tube 103 to the proximal portion 102.

Cart 601 is connected to a proximal portion of a flexible rubber bend 603, the distal portion of the rubber bend 603 is connected to the distal end of the central shaft 105. When no force is applied on the deployment wire 602, cart 601 is pulled toward the distal end of the central shaft 105 and the distal portion is held in its closed configuration.

Once pulling force is applied to the deployment wire 602, by the deployment lever 113, cart 601 in moved reciprocally toward the proximal portion. As a result of said reciprocal movement, the distal portion is transformed from its closed configuration into its open configuration.

Since the central shaft is not moving in relation to tube 103 and not passing through the articulation regions 201,203, lateral and vertical articulation can be performed at any point along the deployment process, including in closed state in which the maneuverability of the distal portion inside the confined space of the patient's abdominal cavity 401 in maximal.

Figure 12A:
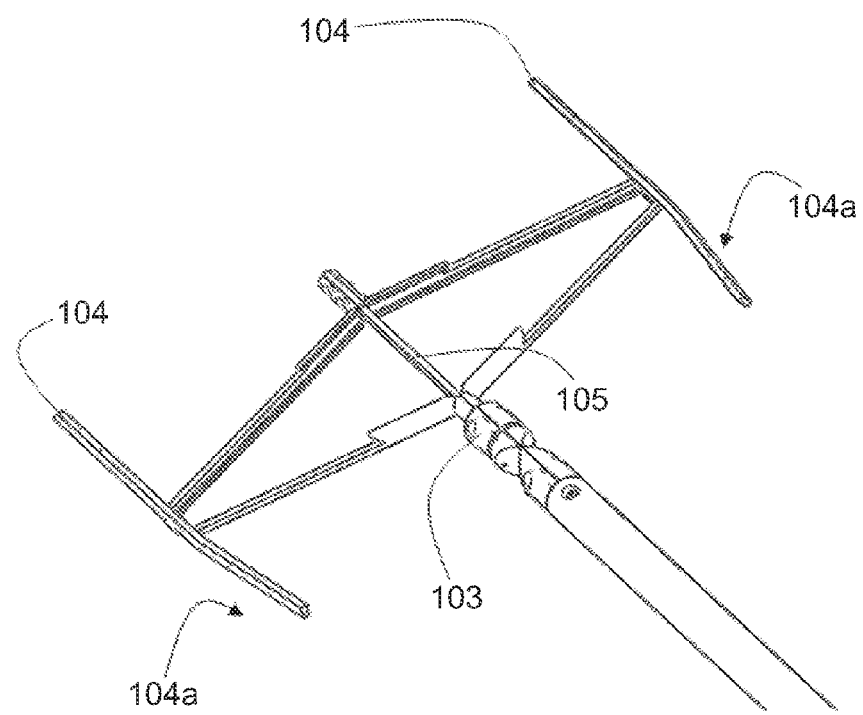
FIGS. 12A-12B and 13A-13C illustrate several embodiments of the present invention in which safe extraction of the distal portion 101 form the patient's abdominal cavity trough trocal 114 is obtained.
Figure 12B:
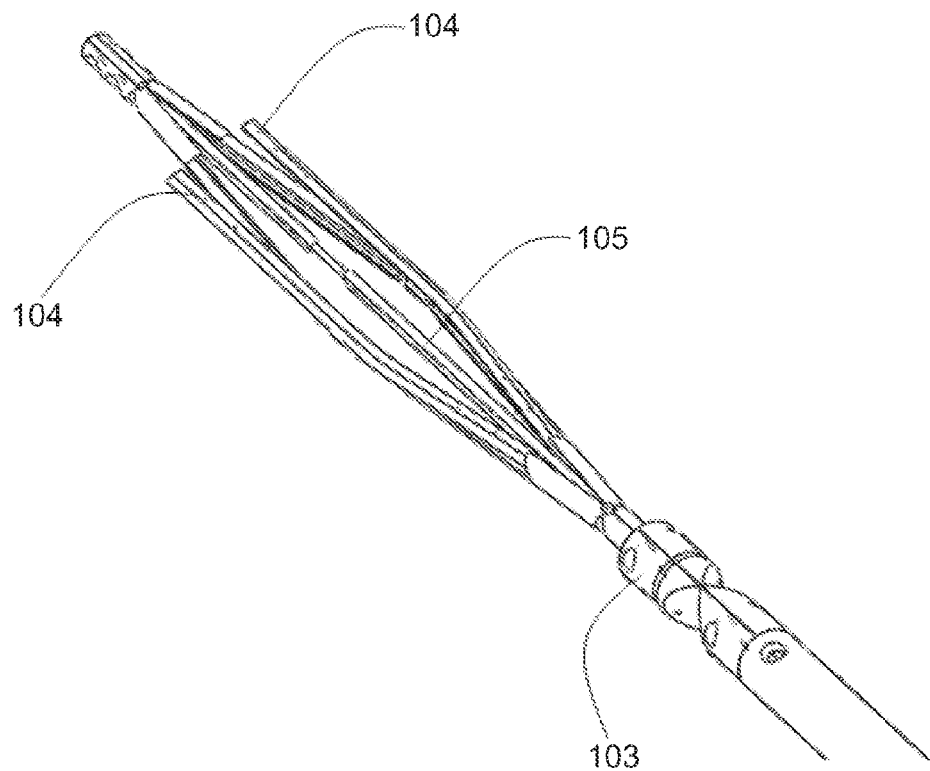

Referance is now made to FIG. 12A-12B, which describe several embodiments of the present invention in which safe extraction of the distal portion 101 from the patient's abdominal cavity through trocar 114 is obtained.

Once the deployment is completed and the distal portion 101 is extracted from the patient's abdominal cavity, the proximal end (104a) of FAs 104 may not enter into the trocar 114;

As a result, the distal portion may be jammed at the trocar 114 or may be broken (i.e jamming situation).

According to the embodiment described at FIGS. 12A-12B, the jamming situation is prevented by slightly bending each FA 104 toward the central shaft 105 (FIG. 12A); as a result of such bending, once the distal portion is in its closed configuration, the proximal ends 104a of FAs 104 is in contact with each other and adjacent to the central shaft 105 (FIG. 12B). In such a manner, a correct entrance of the proximal portion 104a of the FAs 104 into the trocar 114, during extraction, is obtained.

Figure 13A:
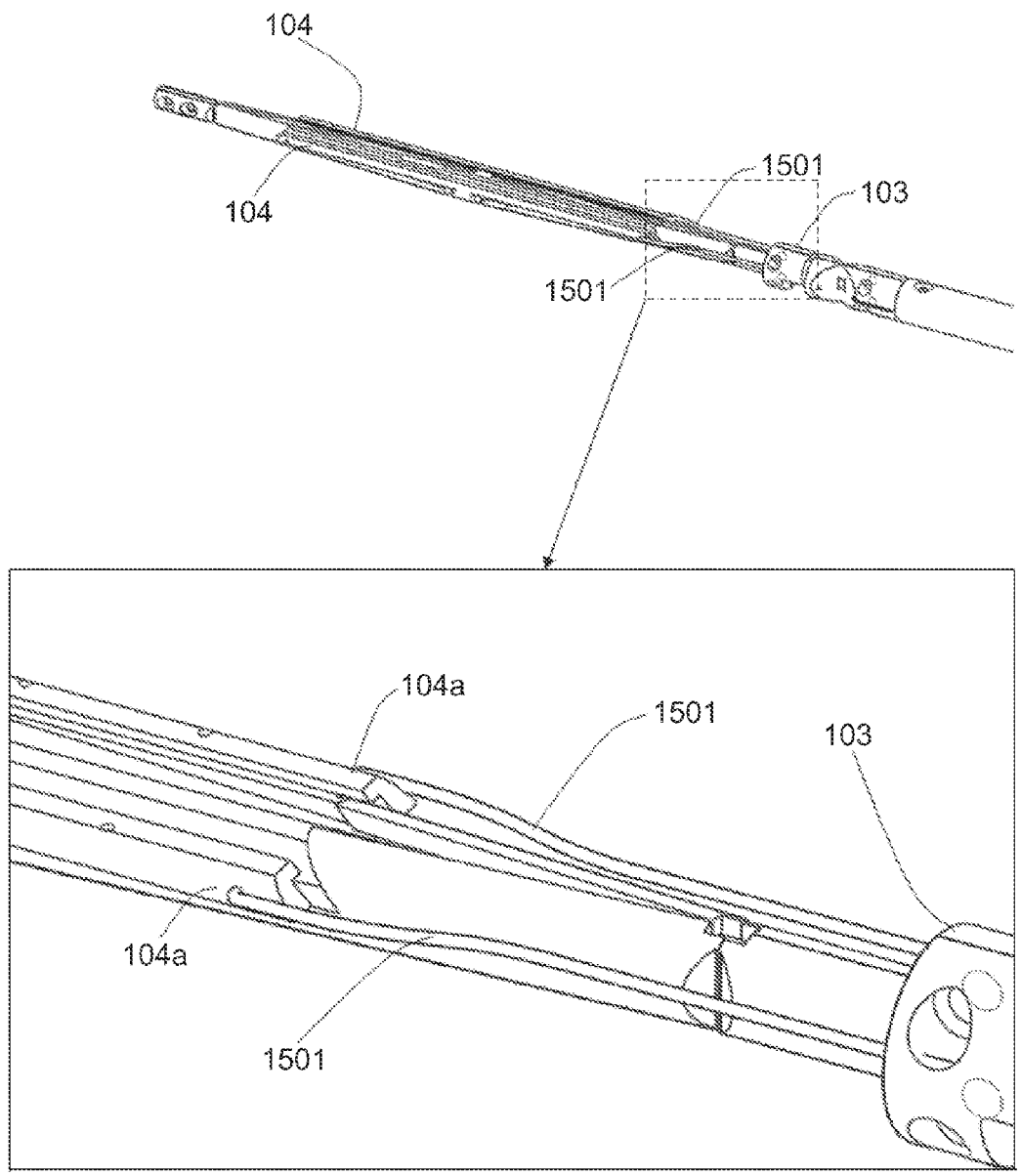

According to another embodiment, said jamming situation is prevented by the use of a flexibel wire 1501. Such an embodiment is described in FIG. 13A-13C.

The jamming situation is prevented by connecting the proximal end 104a of each FA 104 to the distal end of tube 103 by a flexible wire 1501. Once the distal portion 101 is extracted trough the trocar 114, wire 1501 guides the FAs 104 into trocar 114 and prevents them from being jammed outside trocar 114.

Figure 13B:
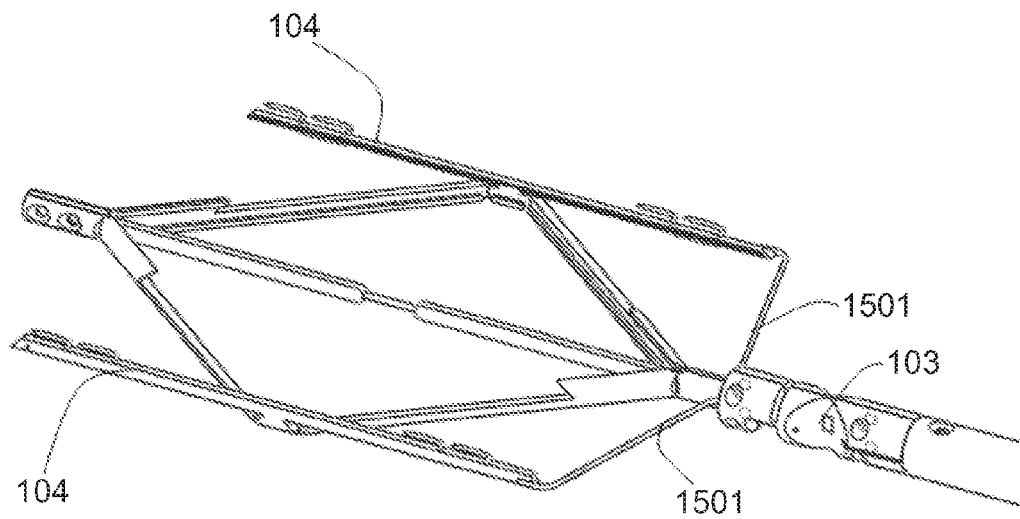
Figure 13C:
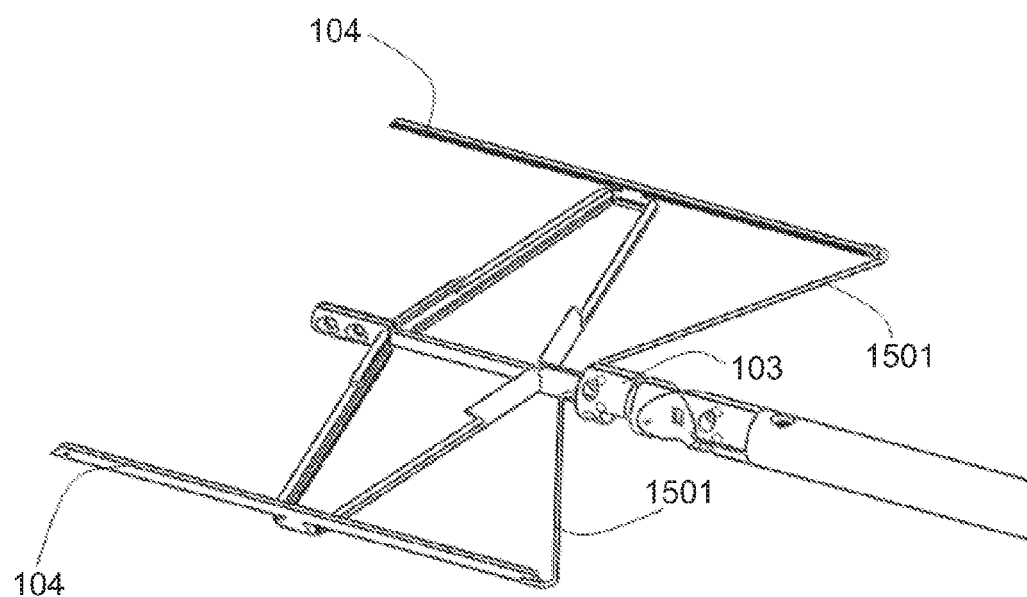

When the distal portion 101 is transferred into its open state, wire 1501 is stretched such that proper deployment is enabled (FIGS. 13B-13C). Additional wires may be added between the distal ends of each FA 104 and the distal end of the central shaft 105 in order to add stability to the system.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for closing an aperture in a biological tissue comprising:
 a handle;
 an elongate shaft connected to the handle, wherein the elongate shaft is rigid during insertion of the system into a subject and flexible during attachment of a surgical implant to the biological tissue;
 a deployment scaffold connected to the elongate shaft, wherein the deployment scaffold is configured to deploy a surgical implant, includes a pair of opposed arms defining a plane, and the deployment scaffold articulates laterally relative to a longitudinal axis of the elongate shaft and along the plane defined by the arms, the arms transitionable between a closed configuration defining a first space between the arms and a deployed configuration defining a second space between the arms that is greater than the first space, the arms remaining parallel to one another as the arms transition between the closed and deployed configurations; and a plurality of attachment members configured to releasably retain a surgical implant to the deployment scaffold.

2. The system according to claim 1, wherein the deployment scaffold is configured to releasably retain a surgical implant.

3. The system according to claim 1, wherein the deployment scaffold is configured to attach a surgical implant to the biological tissue.

4. The system according to claim 1, wherein the elongate shaft comprises:
 first and second rigid portions connected by a flexible portion, wherein the first and second rigid portions are interlocked to provide rigidity to the elongate shaft.

5. The system according to claim 1, wherein one or more of the arms is configured to hold a surgical implant.

6. The system according to claim 5, wherein the arms are flexible.

7. The system according to claim 5, wherein the arms are rigid.

8. The system according to claim 1, wherein the scaffold comprises:
 a frame having the arms hingedly connected thereto,
 wherein the arms are configured to move between the closed configuration and a plurality of deployed configurations;
 wherein the frame is configured to hold a surgical implant.

9. The system according to claim 1, wherein the deployment scaffold is configured to allow for deployment of a surgical implant and retraction of a surgical implant while positioned within a patient's body.

10. The system according to claim 1, wherein the deployment scaffold is configured to allow for a plurality of deployment configurations.

11. The system according to claim 1, wherein the deployment scaffold comprises an articulating member that allows for adjustment of a position and an orientation of a surgical implant relative to an aperture in the biological tissue.

12. The system according to claim 11, wherein the articulating member comprises wires that are configured to control adjustment of a surgical implant.

13. The system according to claim 1, further comprising a surgical implant.

14. The system according to claim 13, wherein the surgical implant is a patch.

15. The system according to claim 14, wherein the patch is porous.

16. The system according to claim 14, wherein the patch is non-porous.

17. The system according to claim 14, wherein the patch is comprised of surgical mesh.

18. The system according to claim 1, wherein the aperture in the biological tissue is an aperture in an abdominal wall.

19. The system of claim 1, wherein a surgical implant coupled to the arms transitions towards a planar configuration when the arms transition towards the deployed configuration.

20. The system of claim 1, wherein the attachment members are configured to attach a surgical implant to biological tissue.

* * * * *